(12) United States Patent
Greenfield

(10) Patent No.: US 11,813,367 B2
(45) Date of Patent: Nov. 14, 2023

(54) TREATMENT AND AGITATION DEVICE FOR ULTRAVIOLET, TEMPERATURE AND GASEOUS CONTROLLED STERILIZATION, CURING AND TREATMENT OF AGRICULTURAL PRODUCTS INCLUDING CANNABIS, AND METHODS FOR TREATMENT

(71) Applicant: Jon Greenfield, Los Angeles, CA (US)

(72) Inventor: Jon Greenfield, Los Angeles, CA (US)

( * ) Notice: Subject to any disclaimer, the term of this patent is extended or adjusted under 35 U.S.C. 154(b) by 174 days.

(21) Appl. No.: 17/507,706

(22) Filed: Oct. 21, 2021

(65) Prior Publication Data

US 2022/0040341 A1 Feb. 10, 2022

Related U.S. Application Data

(62) Division of application No. 16/748,670, filed on Jan. 21, 2020, now Pat. No. 11,154,627.

(60) Provisional application No. 62/794,960, filed on Jan. 21, 2019.

(51) Int. Cl.
| | |
|---|---|
| *A61L 2/00* | (2006.01) |
| *A61L 2/26* | (2006.01) |
| *B01J 19/00* | (2006.01) |
| *B01J 19/12* | (2006.01) |

(52) U.S. Cl.
CPC .............. *A61L 2/0047* (2013.01); *A61L 2/26* (2013.01); *B01J 19/0066* (2013.01); *B01J 19/124* (2013.01); *A61L 2202/14* (2013.01); *A61L 2202/20* (2013.01)

(58) Field of Classification Search
None
See application file for complete search history.

(56) References Cited

U.S. PATENT DOCUMENTS

| 3,767,909 A * | 10/1973 | Bell ....................... B60Q 1/326 |
| | | 362/500 |
| 5,567,616 A * | 10/1996 | Dill, II ...................... A61L 2/10 |
| | | 366/233 |
| 2003/0085111 A1* | 5/2003 | Tabatabaie-Raissi ....................... |
| | | C02F 1/725 |
| | | 422/186 |

FOREIGN PATENT DOCUMENTS

KR   2008001996 U   *   6/2008   ............. G06F 21/54

OTHER PUBLICATIONS

Written English translation of KR 2008001996 provided by USPTO (original document published in 2008) (Year: 2008).*

* cited by examiner

*Primary Examiner* — Holly Kipouros
(74) *Attorney, Agent, or Firm* — Lapple Ubell IP Law, LLP; Matthew Lapple

(57) ABSTRACT

An ultraviolet light sterilization device for treatment of plant materials, having a rotational treatment chamber having an axis of rotation and at least one mechanical agitation element, an ultraviolet light device that is positioned inside the rotational treatment chamber and is further positioned generally parallel to and congruent with the axis of rotation and where the ultraviolet light device and the rotational treatment chamber are connected to one another via a rotational bearing such that the rotational treatment chamber may be rotated about the axis of rotation while the ultraviolet light device does not rotate, and where the ultraviolet light device is electrically coupled to a power source via an electrical cable that passes through an aperture in the rotational bearing.

17 Claims, 20 Drawing Sheets

Synthesis of Various Cannabinoids

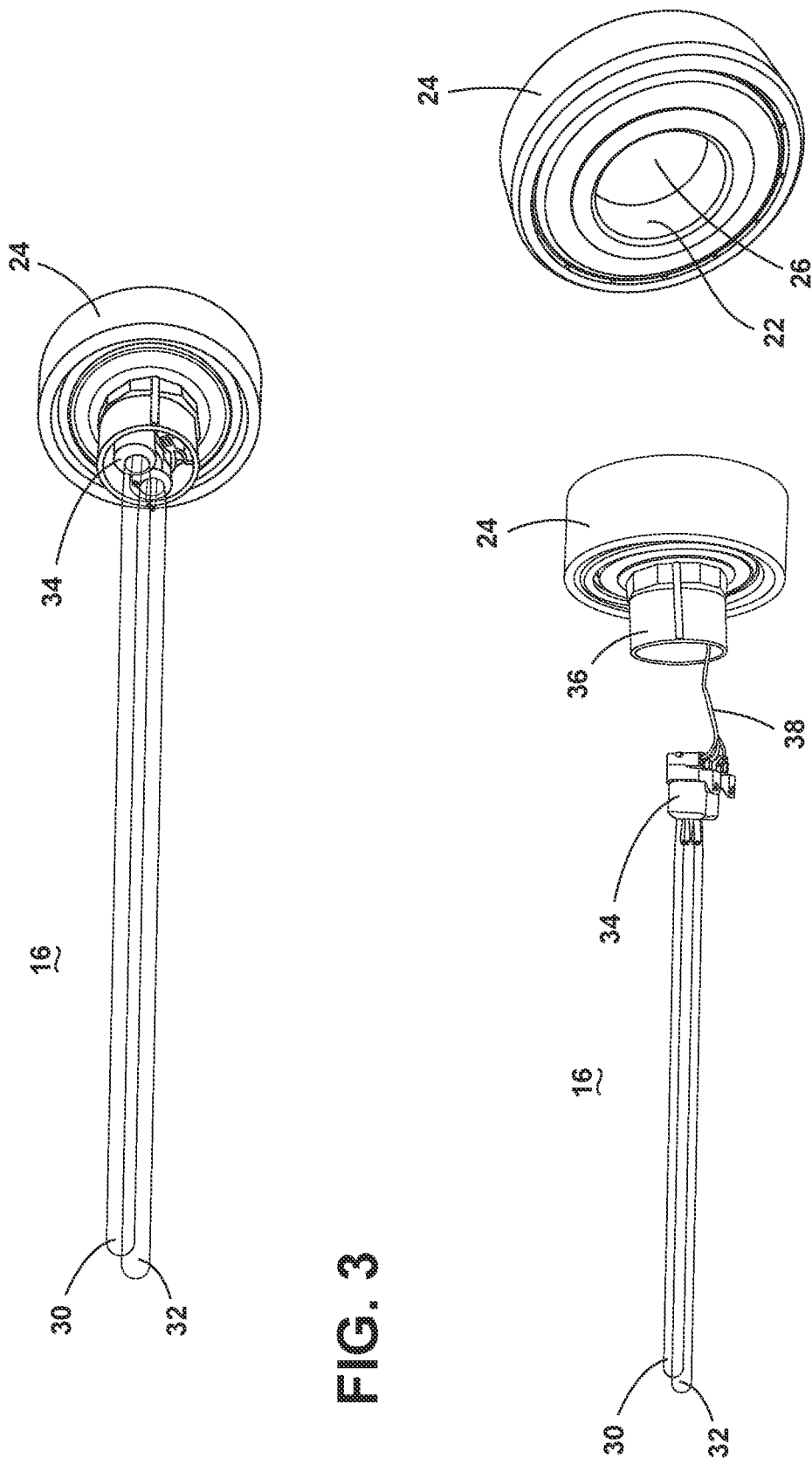

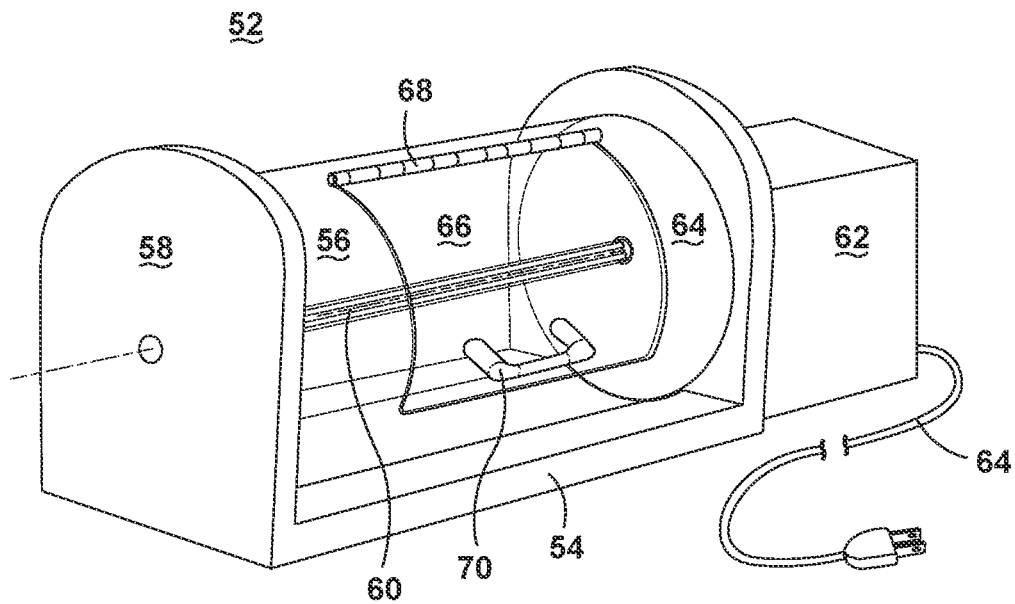
FIG. 7
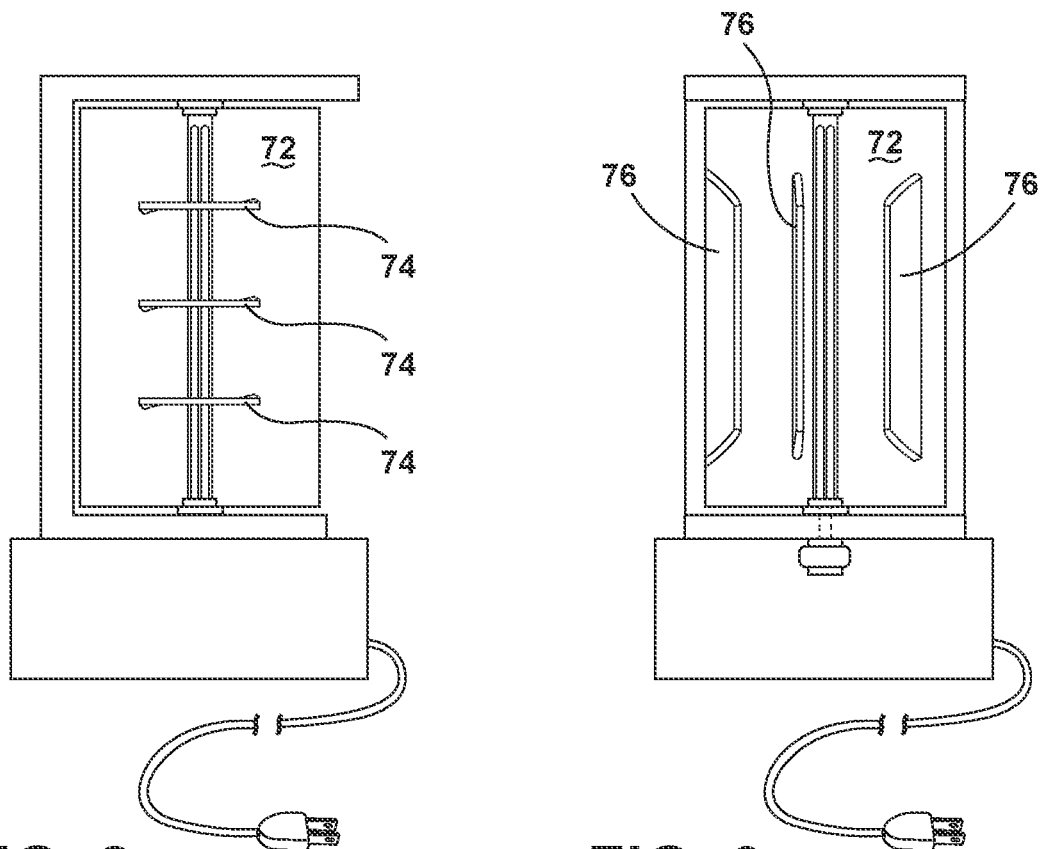
FIG. 8
FIG. 9

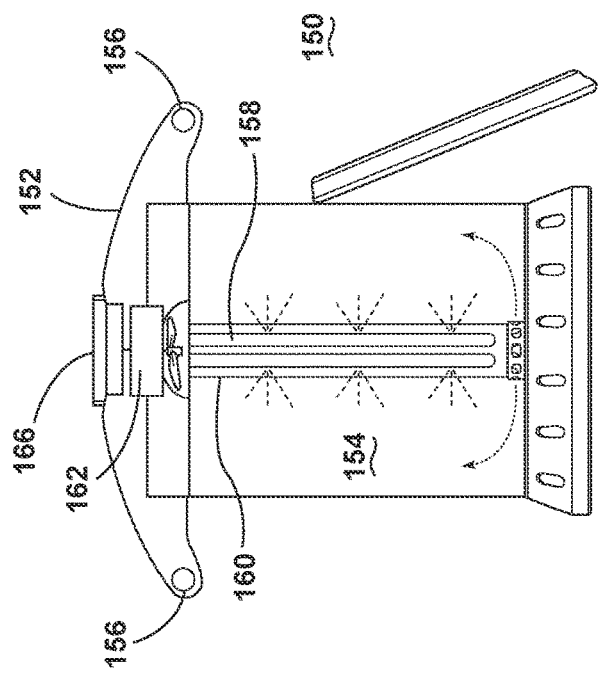
FIG. 26
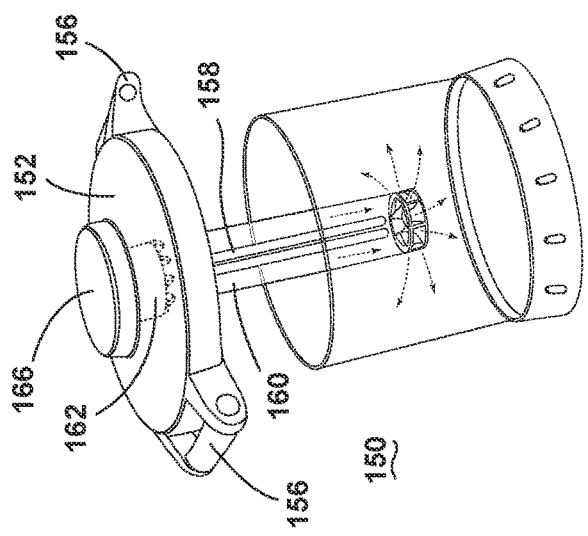
FIG. 28
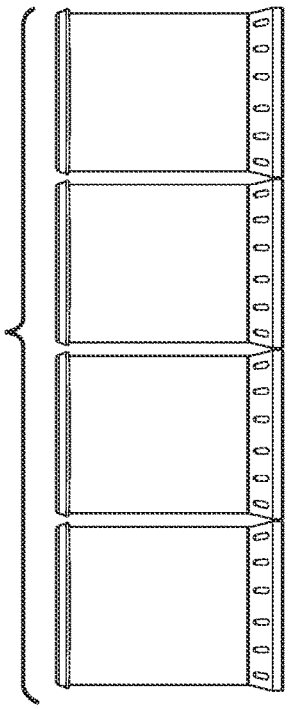
FIG. 27
FIG. 29

TREATMENT AND AGITATION DEVICE FOR ULTRAVIOLET, TEMPERATURE AND GASEOUS CONTROLLED STERILIZATION, CURING AND TREATMENT OF AGRICULTURAL PRODUCTS INCLUDING CANNABIS, AND METHODS FOR TREATMENT

CROSS-REFERENCE TO RELATED APPLICATIONS

This application is a divisional of U.S. patent application Ser. No. 16/748,670; filed on Jan. 21, 2020; and further claims the benefit of U.S. Provisional Patent Application No. 62/794,960, filed on Jan. 21, 2019; both of which are incorporated by reference herein in their entirety.

FIELD OF THE DISCLOSURE

The embodiments of the described invention relate generally to a treatment device for containing and agitating agricultural products, in order to provide controlled artificial exposure to ultraviolet light, variation of wavelengths and periods of time for that artificial exposure to ultraviolet light, temperature variation, and/or gaseous environments, for purposes of sterilizing and/or artificially curing agricultural products, including but not limited to cannabis.

BACKGROUND

Agricultural products intended for human consumption are often treated in various ways prior to consumption. For example, leafy agricultural products may require treatment for elimination or reduction of bacteria, viruses, molds, spores, mildews, mites, or insects that can cause human illness, or which detract from the desirability, marketability, or appearance of the agricultural products.

Additionally, it may be desirable to treat agricultural products for purposes of curing or altering characteristics of the agricultural product. Such curing or alteration can include modification of moisture content, or the chemical composition of the agricultural product. Such curing or alteration may be for the purposes of artificially accelerating, or arresting, certain natural degradation processes by, for example, the application of various wavelengths of UV or natural light, heat, oxygen, or other gasses.

For purposes of this application, the electromagnetic spectrum of ultraviolet radiation (UVR), defined most broadly as 10-400 nanometers, can be subdivided into a number of ranges recommended by the ISO standard ISO-21348. Ultraviolet A, or "UVA", is radiation with a wavelength of between 315-400 nm, with a photon energy of 3.10-3.94 eV (0.497-0.631 aJ). UVA is also commonly known as "long-wave UV," or "black light." UVA is generally not absorbed by the ozone layer and instead reaches the surface of the earth with normal sunlight.

Ultraviolet B or "UVB", is radiation with a wavelength of between 280-315 nm, with a photon energy of 3.94-4.43 eV (0.631-0.710 aJ). UVB is also commonly known as "medium-wave UV." UVB is mostly absorbed by the ozone layer. As such, certain natural processes occur in agricultural products due to exposure to UVB; however, the effects may be limited by the amount and timing of such exposure in a natural environment.

Ultraviolet C or "UVC", is radiation with a wavelength of between 100-280 nm, with a photon energy of 4.43-12.4 eV (0.710-1.987 aJ). UVC is commonly known as "short-wave UV" or "germicidal UV." It is capable of destroying most bacteria, viruses, molds, and other pathogens, by destroying nucleic acids and disrupting DNA, leaving them unable to perform vital cellular functions. However, UVC is completely absorbed by the ozone layer and atmosphere, and is thus not naturally occurring with respect to agricultural products. It is generally reported that the most effective germicidal properties occur in the range of 240-280 nm, with peak DNA absorption at about 260 nm.

UVR may be blocked, or able to pass through, various forms of glass and plastic. For example, common soda-lime glass is partially transparent to UVA but is opaque to shorter wavelengths, whereas fused quartz glass, depending on quality, can be transparent, to some extent, even to UVC wavelengths. Ordinary window glass passes about 90% of the light above 350 nm, but blocks over 90% of the light below 300 nm. Wood's glass is a nickel-bearing form of glass with a deep blue-purple color that blocks most visible light and passes ultraviolet light.

Germicidal UV for disinfection is most typically generated by a mercury-vapor lamp. Low-pressure mercury vapor has a strong emission line at 254 nm, which is within the range of wavelengths that demonstrate strong disinfection effect. The optimal wavelengths for disinfection are close to 270 nm. The dosage of UVC light necessary to sterilize various pathogens are still subject to some study, but a useful reference table for the required dosages are included in *UV Dose Required to Achieve Incremental Log Inactivation of Bacteria, Protozoa and Viruses*, Gabriel Chevrefils, et. al., IUVA News/Vol. 8 No. 1, pp. 38-45 (March 2006), (hereinafter "Chevrefils") which is hereby incorporated by reference.

UV Lamps are typically either amalgam or medium-pressure lamps. Low-pressure UV lamps offer high efficiencies (approx. 35% UVC) but lower power, typically 1 W/cm power density (power per unit of arc length). Amalgam UV lamps are a higher-power version of low-pressure lamps. They operate at higher temperatures and have a lifetime of up to 16,000 hours. Their efficiency is slightly lower than that of traditional low-pressure lamps (approx. 33% UVC output) and power density is approximately 2-3 W/cm. Medium-pressure UV lamps have a broad and pronounced peak-line spectrum and a high radiation output but lower UVC efficiency of 10% or less. Typical power density is 30 $W/cm^3$ or greater.

Depending on the quartz glass used for the lamp body, low-pressure and amalgam UV emit radiation at 254 nm and also at 185 nm, which has chemical effects. UV radiation at 185 nm is used to generate ozone.

Recent developments in LED technology have led to commercially available UVC LEDs. UVC LEDs use semiconductors to emit light between 255 nm-280 nm. The wavelength emission is tunable by adjusting the material of the semiconductor. Low power consumption of semiconductors can also result in UV disinfection systems powered by small solar cells.

Examples of prior art devices for using ultraviolet light to sterilize some agricultural products are known. However, each has disadvantages.

Some prior devices include a conveyor belt, moving under one or more UV lamps, for moving agricultural products under lamps. Others include a drum which rotates and tumbles agricultural products, or which use a screw auger. Such devices typically have an externally positioned UV light, outside of the drum containing agricultural products. UV light is then directed into the drum via one or more reflectors. Disadvantages of such devices include an inability to ensure sufficient UV exposure on the agricultural products, caused by attenuation of UV light passing through glass, plastic, oxygen and/or ambient air, and off of reflectors, when passing from the UV light source to the level of the device where the agricultural products are present. Further, such devices often provide inadequate tumbling or turning of leafy agricultural products with irregularly shaped surfaces, to be able to adequately and uniformly sterilize the surfaces of such leafy agricultural products. Moreover, known devices provide limited ability to control exposure to different thermal environments, or different gaseous environments, for the purpose of enhancing sterilization, or artificially causing or accelerating certain curing processes.

Agricultural products should be understood in its broadest sense, to include, without limitation, leaves, flowers, bracts, fruit, nuts, stems, roots, tubers, and any other parts of a plant that has commercial value.

One such agricultural product, to which certain embodiments of the present disclosure are directed, is Cannabis. Cannabis, also commonly known as marijuana, is a flowering plant that includes three species or sub-species, namely sativa, indica and ruderalis. A closely related agricultural plant, which is sometimes also called "cannabis", is what is otherwise known as "hemp" or "industrial hemp." The cannabis plant is indigenous to Central Asia and the Indian Subcontinent. Cannabis has long been used for hemp fiber, for oils, for medicinal purposes and as a recreational drug. Cannabis plants produce a group of chemicals called cannabinoids. The majority of these compounds are secreted by glandular trichomes that occur abundantly on the floral calyxes and bracts of female cannabis plants. When used by humans medicinally or recreationally, cannabis can be consumed by a variety of routes, including vaporizing or smoking dried flower buds and leaf portions, resins, extracted oils or waxes.

The most well-known cannabinoid is tetrahydrocannabinol, often abbreviated as "THC." The chemical formula for THC is $C_{21}H_{30}O_2$ and it has the following chemical structure:

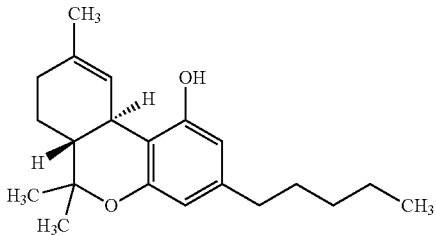 [SMILES: CCCCCc1cc(O)c2c(c1)OC(C)(C)[C@@H]1CCC(C)=C[C@@H]21]

THC is widely recognized as the principal psychoactive constituent in cannabis. THC has a very low solubility in water, but good solubility in most organic solvents, specifically lipids and alcohols.

The cannabis plant produces hundreds of other cannabinoids, terpenoids and other compounds that are only beginning to be identified, studied and categorized. One generally recognized cannabinoid that has medical efficacy is Cannabidiol ("CBD"). It is a major constituent of the plant, second to THC, and represents up to 40% by weight, in its extracts. Compared with THC, CBD is not psychoactive in healthy individuals, and is considered to have a wider scope of medical applications than THC, including for epilepsy, multiple sclerosis spasms, anxiety disorders, bipolar disorder, schizophrenia, nausea, convulsion and inflammation, as well as inhibiting cancer cell growth.

Another known cannabinoid is Cannabinol ("CBN"). CBN is a non-psychoactive cannabinoid found only in trace amounts in growing or recently harvested Cannabis, but is mostly found in aged Cannabis. Pharmacologically relevant quantities of CBN are formed as a metabolite of tetrahydrocannabinol THC. CBN acts as a partial agonist at the CB1 receptors, but has a higher affinity to CB2 receptors; however, it has lower affinities relative to THC. Anecdotally, CBN is believed to be sleep-inducing.

Unlike other cannabinoids, CBN does not stem directly from cannabigerol ("CBG") or cannabigerolic acid ("CBGA"), but rather is the degraded product of tetrahydrocannabinolic acid ("THCA"). If harvested cannabis is exposed to oxygen and/or ultraviolet light (for example, in sunlight) for a prolonged period of time, THCA will convert to cannabinolic acid ("CBNA"). CBN is then formed by decarboxylation of CBNA. There has been no known comprehensive investigation of how various wavelengths of light affect the chemical conversion of one cannabinoid to another. However, is it suspected that various wavelengths of light may be involved in some of these processes.

It is also believed by many researchers that many of the other cannabinoids, terpenoids and other compounds may have important health benefits and/or be capable of treating certain human diseases.

In the early twentieth century, it became illegal in most of the world to cultivate or possess cannabis. However, within the last decade, some states and nations have begun to legalize the cultivation, possession and use of cannabis for medical purposes. Currently, the use of medical marijuana is decriminalized or legalized in many U.S. states. Cannabis is used to reduce nausea and vomiting during chemotherapy, to improve appetite in people with HIV/AIDS, to treat chronic pain, and help with muscle spasms. Other possible medical uses, which are sometimes disputed, include treatment of multiple sclerosis, AIDS wasting syndrome, epilepsy, rheumatoid arthritis, glaucoma, PTSD, depression and generalized anxiety.

Further, within the last five years, several states in the United States have legalized or decriminalized the cultivation, possession and use of Cannabis for recreational purposes. It is therefore estimated by many experts that cannabis consumption, for both medical and recreational purposes, will increase over the coming years.

Accordingly, there is a need for a treatment and agitation device for ultraviolet, temperature and gaseous controlled sterilization, curing and treatment of agricultural products including cannabis, that addresses the issues and disadvantages of prior art devices discussed above.

SUMMARY

Embodiments of the present invention address the needs described above and relate to a device and method of use for treating, aging, curing or sterilizing agricultural products using a central UV light source that may provide varied UV wavelengths, and further using gas and temperature control, and further providing mechanical and gas agitation of the agricultural products to assist in the treatment, aging, curing or sterilizing processes.

BRIEF DESCRIPTION OF THE DRAWINGS

In the descriptions that follow, like parts or steps are marked throughout the specification and drawings with the same numerals, respectively. The drawing figures are not necessarily drawn to scale and certain figures may be shown in exaggerated or generalized form in the interest of clarity and conciseness. The disclosure itself, however, as well as a preferred mode of use, further objectives and advantages thereof, will be best understood by reference to the following detailed description of illustrative embodiments when read in conjunction with the accompanying drawings, wherein:

FIG. 3 is a side perspective illustration of an embodiment of the center light column of an embodiment of the ultraviolet treatment device described herein;

FIG. 4 is a de-constructed side perspective illustration of the center light column of an embodiment of the ultraviolet treatment device described herein showing the ultraviolet light fixture removed from the bearing mount;

FIG. 5 is a side perspective illustration of the bearing mount for the center light column of an embodiment of the ultraviolet treatment device described herein;

FIG. 7 is a side perspective illustration of a second embodiment of the ultraviolet treatment device described herein;

FIG. 8 is a schematic side illustration of the second embodiment of the ultraviolet treatment device described herein with a first configuration of a mechanical agitator mechanism;

FIG. 9 is a schematic side illustration of the second embodiment of the ultraviolet treatment device described herein with an alternate configuration of the mechanical agitator mechanism;

FIG. 26 is a perspective view of a sixth embodiment of the device showing an integrated drum lid/light fixture/forced agitation gas pathway partially detached from the drum;

FIG. 27 is a side view of the sixth embodiment of the device showing UV light emanating from the central UV light source in dashed lines, and forced gas for agitation exiting the bottom of the column in dotted lines;

FIG. 28 is a close-up, cutaway, side perspective view of the column showing the forced agitation gas pathway in dotted lines;

FIG. 29 illustrates that multiple, identically shaped drums can be readied in advance with agricultural product, for attachment to the working portion of the device;

DETAILED DESCRIPTION OF THE EMBODIMENTS

Figure 1:
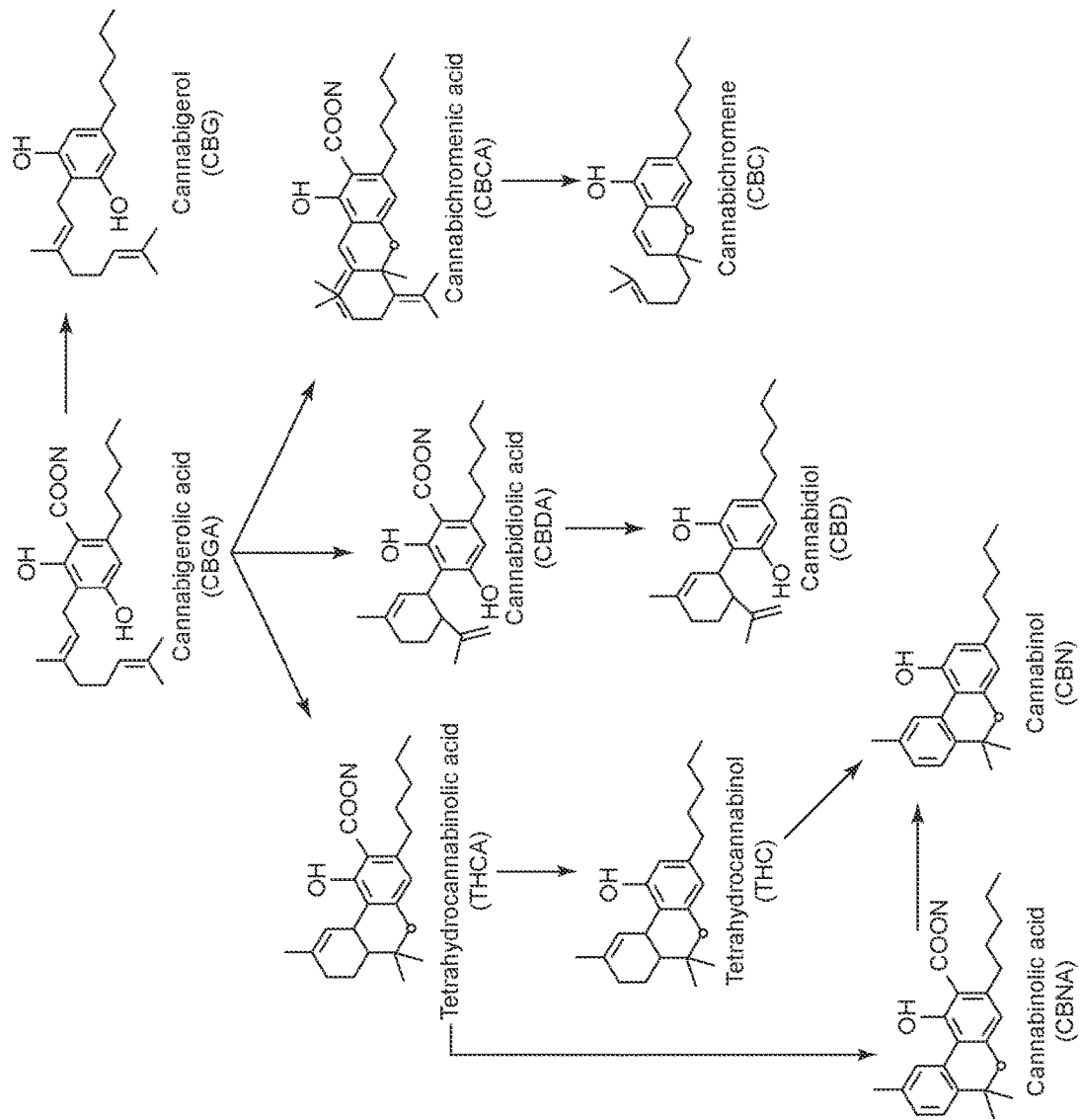
FIG. 1 illustrates some suspected pathways for synthesis of various cannabinoids, some of which may involve exposure to various wavelengths of light.

The description that follows is presented to enable one skilled in the art to make and use the present invention, and is provided in the context of a particular application and its requirements. Various modifications to the disclosed embodiments will be apparent to those skilled in the art, and the general principles discussed may be applied to other embodiments and applications without departing from the scope and spirit of the invention. Therefore, the invention is not intended to be limited to the embodiments disclosed, but the invention is to be given the largest possible scope which is consistent with the principles and features described herein.

Embodiments disclosed herein relate to a device for sterilizing, sanitizing, and/or curing agricultural products with exposure to ultraviolet light, of a variety of different wavelengths, including UVA, UVB and UVC. It has been identified that curing (and/or aging) occurs when agricultural products are subjected to periods of time and environmental conditions prior to, or after, processing. For example, tobacco is cured, spices are dried, and wine and cheese are aged. These processes rely on exposure to environmental conditions which give the processor limited control. Expose (or prevention of exposure) to air, oxygen, nitrogen, temperature, UV or regular light are all involved. Embodiments of the disclosed device allows precise control of these environmental conditions to determine which factors are important to the process. Embodiments of the device allows the manipulation of the environment of the agricultural material being processed to determine which factors are important to the process. It is expected that further investigation and experimentation will occur with embodiments of the device to determine improved processes for aging and curing of various agricultural products, including which wavelengths of light (including visible light, UV light, and/or infra-red light), or combinations of wavelengths or light, what intensity of light, which gases, how much exposure time is necessary, as well as other potential factors that can be controlled.

It is known that, with respect to harvested cannabis, THC converts to CBN when exposed to UV light and oxygen. Embodiments of the device will allow a user to determine which wavelengths of light, what concentrations of oxygen, what time is required, and whether subsequent exposure to different wavelengths of light or other gases or varying temperatures will change (improve or interfere) with the process of conversion of THC to CBN. In certain embodiments, the UV light source is tunable, enabling a user to select particular frequencies to accomplish treatment goals, such as sterilization, or modification of the moisture content or chemical composition of the agricultural product being treated.

It should be understood that curing of agricultural products can involve various steps or stages. Embodiments disclosed herein allow a user to control exposure of the agricultural products to various forms of radiation (for example x-rays, microwave, UV, visible light, infrared and/or radio waves), varying temperature, varying gases (for example air, oxygen, nitrogen, carbon dioxide), including gasses containing particulates, such as smoke, all in the same container, over varying periods of time, so that all of the steps of any particular curing regimen can be done in the same device and the agricultural products does not have to be moved between machines during the process.

Further, in embodiment disclosed herein, while the descriptions below typically refer to a central UV light source, it should be understood that this central UV light source can be replaced with various other sources of wavelength radiation to generate x-rays, microwaves, UV, visible light, infrared and/or radio waves, or some combination thereof, to achieve desired treatment and curing regimens.

For example, there are radiation devices for delivery to various parts of the body, including bulbs and/or LED's, which can be placed into a bulb container to include in the embodiments disclosed herein. Further, microwave bulbs are available for use in microwave ovens and could be used in place of the otherwise described central UV light source.

In the embodiments discussed herein, it is intended that heat can be applied independently of air, UV light or smoke. The various steps necessary to cure can be done simultaneously or in succession. Optimum times can be determined for each step or the process. Steps can be automated so that the entire process can be done in one container without moving the material.

The curing of various spices and other plant products is based on experience over time and has not been quantified. Disclosed embodiments will allow for the controlled "curing" or "aging" of plant material to determine the optimum treatment of these plant material products for maximum efficiency and efficacy.

The current laboratory certification of Cannabis products require bacterial (and in the future maybe viral) testing. Treatment of consumer products needs to eliminate bacterial contamination.

A main focus of the disclosed embodiments is the use of a central UV light source, typically located inside a drum, in which the agricultural products may be placed. This central UV light source enables better exposure to UV light, and reduced attenuation of UV radiation over the distance between the UV light source and the agricultural product being treated. This is accomplished by the central location of the UV light source, which places the UV light source closer to the agricultural products than known prior art devices. This placement also reduces the number of layers of glass, plastic or air, present in prior art devices, through which the UV rays must pass before reaching the agricultural products being treated. In certain embodiments disclosed herein, the central UV light source is affixed to, or through, the inside diameter of a bearing race, which allows the light source to be centrally located along the axis of the agitation drum, and to be held in a fixed position with respect to the base of the device, while the agitation drum may be rotated around the central UV light source. While other configurations for delivering power to a central light source in a rotatable drum are known to exist in the prior art, they are generally more costly than the bearing race configuration disclosed herein. That said, the embodiments disclosed herein may be modified to include other configurations to provide power to a central light source other than the bearing race configuration disclosed.

Further, the configurations using a central spindle with a bearing race to mount and contain the light source allow for quick and easy modification of the central light source. For example, in each embodiment disclosed herein, it is possible to remove the central UV light source (such as a UV bulb or a series of UV LED's) and to replace them with a light source generating a different frequency of light, such as visible light or infrared light, or some combination thereof. This ability to quickly and easily change the light source—and the resultant light radiated by it—enables the device to be used for a wide and varied number of processes for treatment and curing of agricultural products, and further enables the expected development of new processes to achieve artificial aging, curing, sterilization, and other treatment of agricultural products.

Embodiments disclosed herein, especially those using tunable UV LED's, also all generally enable the wavelengths of the UV light delivered, and the intensity of that light, to be varied in order to achieve and/or develop processes for aging, curing, treatment and sterilization of agricultural products.

The bearing race/central spindle configuration discussed herein also provides for efficient delivery of gas for treatment of agricultural products. For example, in certain of the embodiments disclosed herein, the simplest method of providing oxygen (or other treatment gas) into the canister is to run an oxygen tube through the bearing race/central spindle structure, along the same route that electrical wiring is routed to bring power to the central light source. In some embodiments, a slip ring (in electrical engineering terms) may be used to make an electrical connection through the rotating assembly of the bearing race.

Certain embodiments disclosed herein include the ability to agitate the agricultural products to ensure better UV light exposure to all portions or facets of the agricultural products. This is particularly helpful in treating leafy agricultural products, flowers, bracts, or other irregularly shaped, wrinkled or multiform agricultural products.

Agitation can be accomplished by either mechanical agitation, or gaseous agitation, or both. Mechanical agitation can be any number of paddles, screw augers, or other projecting elements from the inside of a drum, or from the central column containing the UV light source, which when rotated, causes the agricultural products inside the drum to be moved such that all surfaces of the agricultural products are exposed to UV light from the central UV light source. Embodiments disclosed herein generally have the ability for the drum to rotate through a full 360 degree rotation, but it should be understood that the drum may be rotated through a smaller arc and in two different directions, such as, for example 45 degrees clockwise, and then 45 degrees counterclockwise.

Gaseous agitation may comprise forced air driven by a fan, compressed air, or other gas under pressure. In the drawings, for most of the embodiments, a propeller is used to represent controlled injection of gas into the system. That said, any one of a number of mechanisms for gas injection may be used, including, but not limited to pressurized jets with either a fixed or a variable pitch angle.

In some embodiments, the drum containing the agricultural products may be gas tight, to enable injection of certain treatment gasses, such as oxygen, nitrogen, argon, or carbon dioxide, in order to either prevent, or to accelerate certain known biological processes in the agricultural products. For example, and without limitation, when freshly harvested cannabis flower is exposed to UV light and oxygen, the THC and THCA present in the cannabis will degrade to CBN. This curing process typically takes months if allowed to occur naturally. Moreover, such natural processes are difficult to control in order to achieve uniform results. However, in some instances, it may be desirable to accelerate these processes using an embodiment of the apparatus described herein, in order to achieve desired CBN concentrations in a matter of hours or days.

In another example, it may be desirable to control or reduce the amount of THC in harvested cannabis plant material. In some strains of cannabis, the percentage of THC is 3%. However, under a current understanding of federal and state law, in order for the cannabis (or extracted oil) to be sold on the CBD market, the THC content has to be below 0.03%. Use of embodiments of the device may enable a user to expose cannabis products to a controlled environment as discussed herein to reduce the THC content below the threshold for sale as a CBD product.

In another example, in the recreational cannabis market, the higher the THC content the more desirable the product. However, in the medical cannabis market, controlling the amount of THC is important for purposes of proper dosage for patients. Use of embodiments of the device disclosed herein may enable a user to control the concentration of THC in an effort to obtain a more consistent product. For instance, if the THC content of a given marijuana product is 60% it may be possible to expose the product for a known period of time and reduce the THC content to 50%.

Certain embodiments disclosed herein include the ability to control the temperature and humidity of the gas injected into the agitation drum. For example, in order to prevent decay, a user may set the device to use cold, humid air to maintain the crispness of leafy vegetables. In other circumstances, a user may set the device to use warmed, dry air, such as to rapidly cure freshly harvested cannabis flower.

With reference to FIG. 1, certain known chemical reactions and transformations of identified cannabinoids that occur with the processing of the cannabis plant are shown. It is believed that light is involved in some of these transformations; however, as of the filing of this application, Applicant is unaware of any extensive investigation has to how light of varying intensities, wavelengths, and exposure times, affect these chemical transformations. It is expected that continued research and experimental use of embodiments of the device disclosed herein will enable the development of processes to artificially cause these and other transformations to occur in plant material, due to varying intensities and wavelengths of light as well as the other conditions discussed herein.

Figure 2:
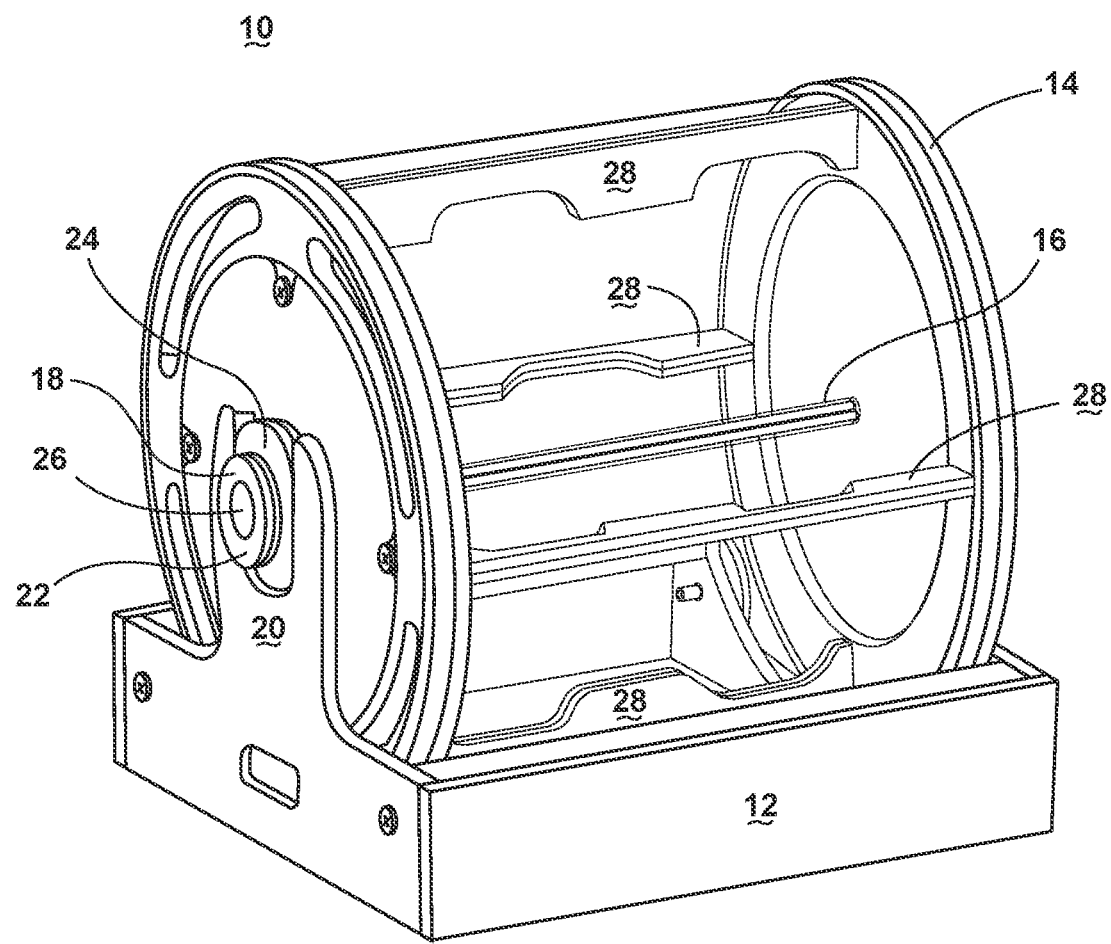
FIG. 2 is a side perspective illustration of a first embodiment of the ultraviolet treatment device described herein.

With reference to FIG. 2, a side perspective of a first embodiment of the ultraviolet treatment device 10 is shown. The ultraviolet treatment device 10 includes a base 12, a drum 14, a central UV light source 16, and a bearing race 18. The drum 14 is mounted on a mount 20 of the base. The drum 14 may be Plexiglas, aluminum, other metal, or any suitable material that can withstand the rotation and heat generated by the device 10. The bearing race 18 is affixed to the drum 14. The bearing race 18 includes an inside race 22 and an outside race 24, which are interlocked to contain a number of lubricated ball bearings (not shown). The central UV light source 16 is affixed to the inside race 22. The bearing race 18 is configured to provide for a central aperture 26, through which wiring to deliver power to the central UV light source 16 may be routed. This central aperture 26 may also be used as a route for tubing for delivery of gas to the interior of the drum 14. In some embodiments, a gas tight seal may be affixed to the central aperture 26, with a port or valve for delivery of gas into the drum.

The drum 14 may be removable from the mount 20, but when it is in its mounted position, as shown, the drum 14 is rotatable about the axis defined along the line generally formed from the center of the central aperture 26, and along the central UV light source 16. This rotation may be accomplished by any conventional means, such as a motor (not shown) mounted in the base 12, a hand crank (not shown), etc., and may be at any desired speed or direction or combination of speed and direction as necessary to achieve suitable agitation of any agricultural materials placed inside the drum 14. The drum 14 may be sealable so that it is gas-tight. The drum 14 has a mechanical agitation device, in this case a plurality of paddles 28. In use, agricultural products may be placed in the drum, up to the level of the central UV light source 16. Upon rotation of the drum 14, the plurality of paddles 28, as well as the rotation of the drum 14, will cause the agricultural products to tumble inside the drum, in a manner similar to a conventional clothes drier. By tumbling, the agricultural products will be better exposed to the UV light radiated by the central UV light source 16 and any treatment gas introduced into the drum 14.

With respect to FIGS. 3-5, further detail of an embodiment of the central UV light source 16 and the bearing race 18 are shown. In this embodiment, the central UV light source 16 includes two UV light bulbs 30, 32, each of which is affixed to a ballast and power assembly 34. In alternative embodiments, not shown, the UV light bulbs may be replaced by a central PCB or other mounting board upon which a plurality of UV emitting light emitting diodes are mounted. The ballast and power assembly 34 is mounted in a central core light socket 36 which is affixed to the inside bearing race 22. The ballast and power assembly 34 has one or more wires 38 extending therefrom, to supply power to the assembly 34. The wires 38 pass through the central aperture 26 and can be operatively connected to a suitable power source (not shown). The embodiment illustrated in FIGS. 3-5 demonstrate how a mechanical bearing is used to allow the light source to remain stationary and to allow simple wiring into the lightbulb to control light intensity and duration. By using a mechanical bearing, the drum filled with agricultural products may rotate while the light source remains intact. This configuration also allows for a stationary covering to cover the central UV light source 16 on its top to prevent material falling on the central UV light source 16 during agitation of the agricultural products. This covering may be of reflective material to increase and control light intensity and exposure in any given direction.

Figure 6:
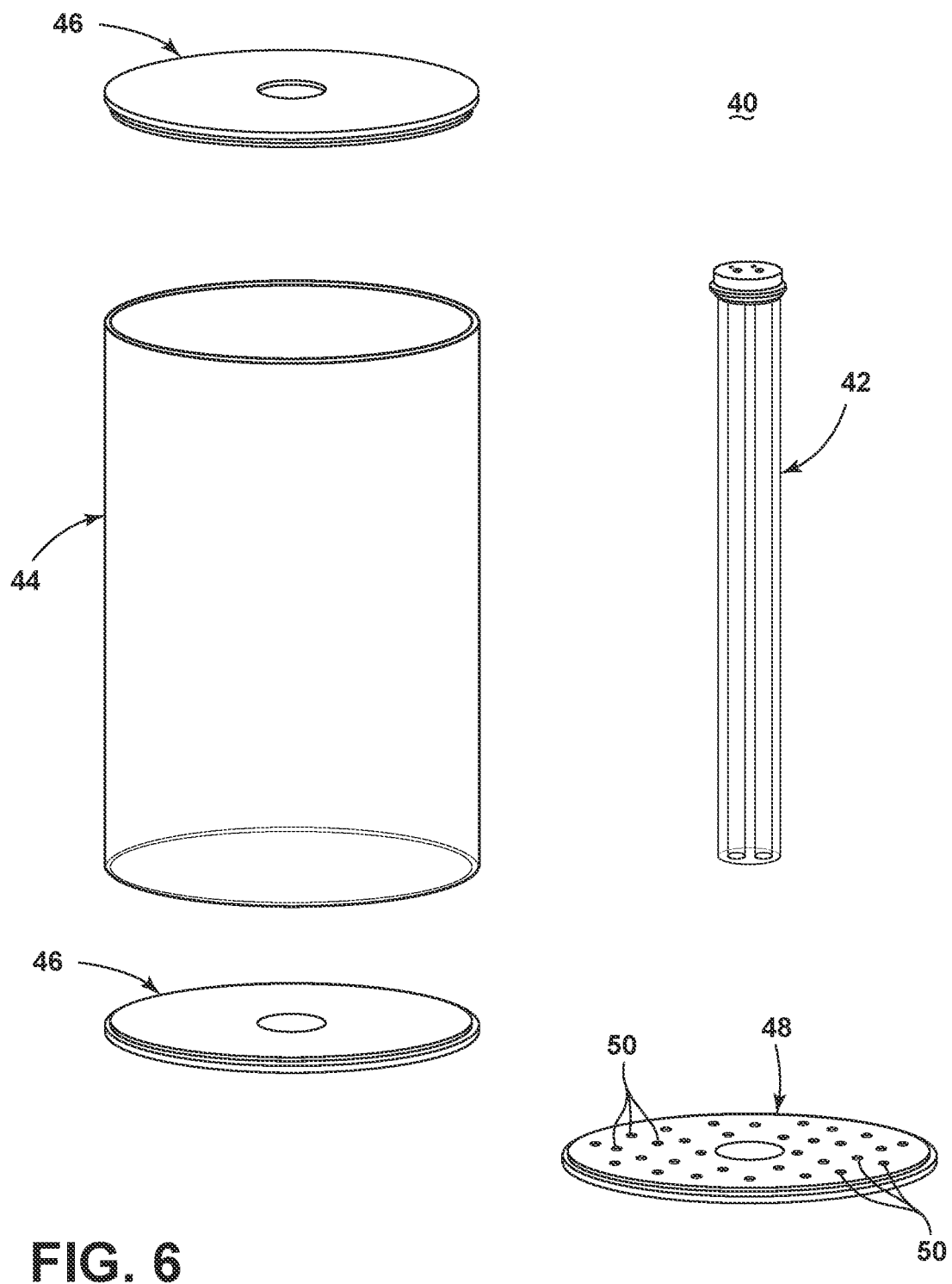
FIG. 6 is a schematic illustration of components of an embodiment of the ultraviolet treatment device described herein, including the central light column, a drum with endcaps, and an optional perforated drum endcap which may be used with certain gaseous injection treatment embodiments disclosed herein.

With respect to FIG. 6, a schematic illustration of components of an embodiment of the ultraviolet treatment device 40. Components include the central light column 42, a containment vessel 44 with endcaps 46, and an optional perforated endcap 48, with perforations 50, which may be attached to the containment vessel 44 in place of one or both of the endcaps 46, and used with certain gaseous injection treatment embodiments disclosed herein. One or more tubes (not shown) can be used and attached to the perforated endcap 48 under the control pumps that will pump air or gas at controlled frequency, duration, and intensity into the containment vessel 44. By doing so a user can control the level of agitation of agricultural products in the containment vessel 44, as well as the direction of agitation, in order to cause tumbling of the agricultural products loaded within the cylindrical containment vessel 44. One embodiment is a fan (not shown) directing air at the perforations in the perforated endcap 48. The direction of each perforation can be controlled (angle of entry and size) by manufacturing to direct air or gas flow. This size of each perforation may control the intensity unless individual air sources are attached to each perforation. Control can be done by restricting air flow (dampering) of one pump or by using individual pumps, valves, or other sources of gas.

With respect to FIGS. 7-9, a second embodiment of the ultraviolet treatment device 52 is shown. The ultraviolet treatment device 52 includes a base 54, a rotatable drum 56 mounted on the mounts 58 of the base 54, a central UV light source 60 and a motor housing 62 containing a motor (not shown). A power cord 64 extends from the motor housing 62 to supply power to the motor. The central UV light source 60 may be mounted and powered as explained throughout this application. Rotation of the drum 56 can be accomplished either from the bottom of the base 54 using rollers (not shown) powered by the motor, or through control of the motor-side end 64 of the drum 56 which then rotates the entire drum 56. The drum 56 has a door 66 that allows for loading and unloading of the agricultural products to be treated. A hinge 68 is on the top of the door 66 with a handle and latch 70 allowing the door to be opened and agricultural products to be removed or inserted into the drum 56 without having to detach the drum 56 from the mounts 58.

As shown in FIG. 8, the second embodiment of the ultraviolet treatment device 52 can be configured with a first configuration of a mechanical agitator mechanism 72 in the form of screws or paddles 74 that rotate around the central UV light source 60. FIG. 9 shows an alternate configuration of the mechanical agitator mechanism 72, in the form of paddles 76 projecting inwardly from the inside of the drum 56.

Figure 10:
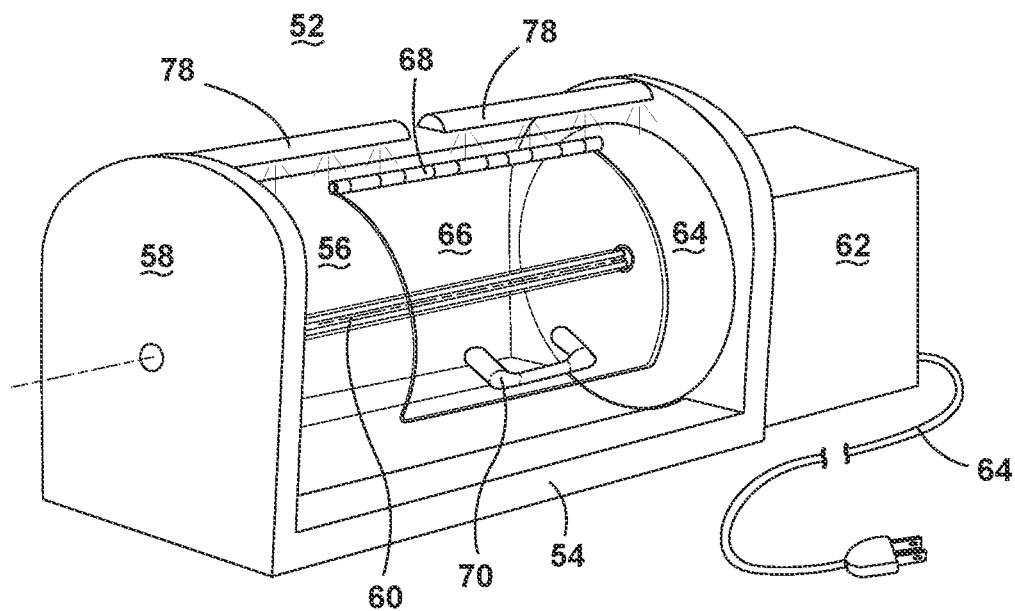
FIG. 10 is a side perspective illustration of the second embodiment of the ultraviolet treatment device described herein with a supplemental ultraviolet light array configured on the outside of the agitator barrel.
Figures 11, 12:
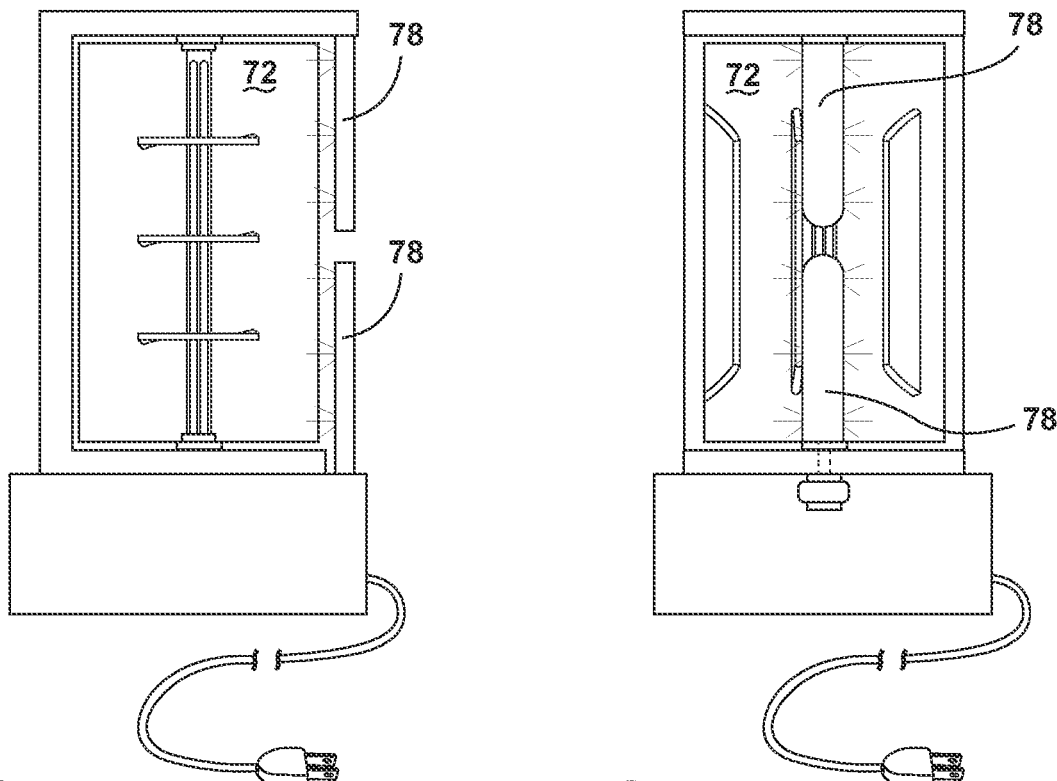
FIG. 11 is a schematic side illustration of the second embodiment of the ultraviolet treatment device, with the supplemental ultraviolet light array, described herein with a first configuration of mechanical agitator mechanism.
FIG. 12 is a schematic side illustration of the second embodiment of the ultraviolet treatment device, with the supplemental ultraviolet light array, described herein with a second configuration of mechanical agitator mechanism.
Figure 13:
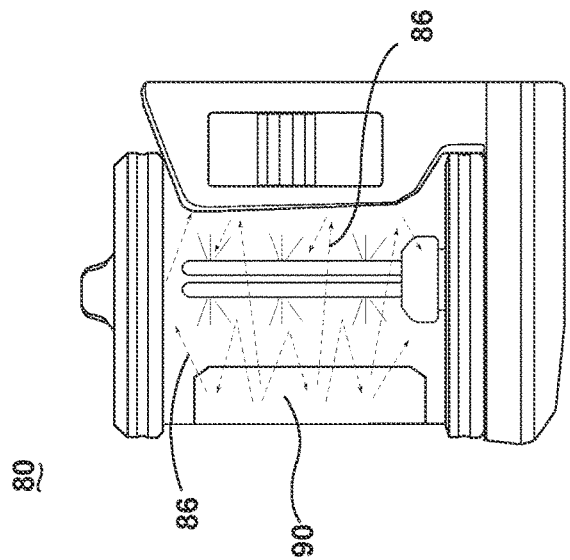
FIG. 13 is a perspective view of a third embodiment of the ultraviolet treatment device described herein with indicators of UV light emanating from a central UV light source.

With respect to FIGS. 10-12, the second embodiment of the ultraviolet treatment device described herein is shown with a supplemental ultraviolet light array 78 configured on the outside of the drum. This configuration allows a user to combine wavelengths of light to research whether combining specific light sources would alter the process and results as opposed to one light source and one wavelength of light. Arrangement of bulbs can be either end to end or side by side. Two bearings can be used, one at either end of the drum with similar or dissimilar radiation sources.

Figure 14:
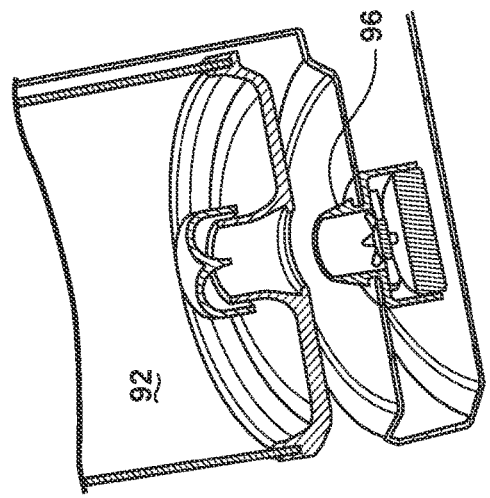
FIG. 14 is a side view of the third embodiment of the ultraviolet treatment device described herein, with dashed lines illustrating reflected UV light.

With respect to FIGS. 13-16, a third embodiment of the ultraviolet treatment device 80 is shown, with indicators of UV light 82 emanating from a central UV light source 84. In FIG. 14, this emanating UV light 82 is further shown reflecting 86 off of internal reflectors 90 on the interior of the drum 92. The drum 92 is mounted on a base 94, that contains a rotation mechanism (not shown) such as a motor, to enable rotation of the drum 92 on an axis defined by the line of the central UV light source 84. Reflectors can be used on the walls of the drum 92 in any of the configurations presented in this patent application.

Figure 15:
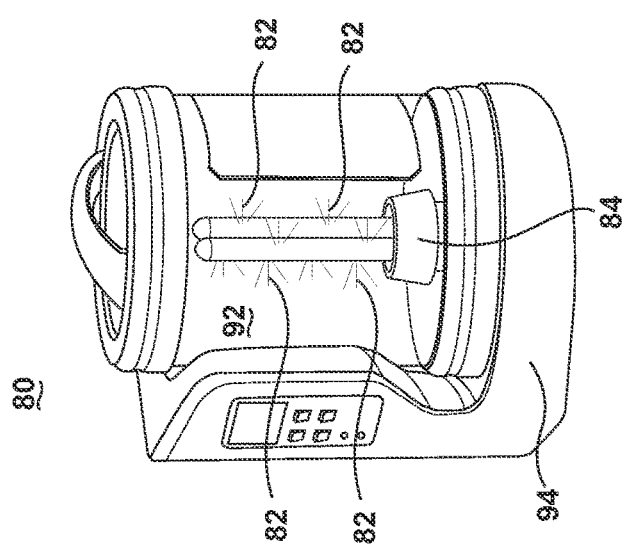
FIG. 15 is a cutaway detail illustration of the upwardly projecting connection point between the agitator drum and the base of the third embodiment device, showing a side view of a rotatable propeller and dashed arrows illustrating gas flow generated by the rotatable propeller.
Figure 16:
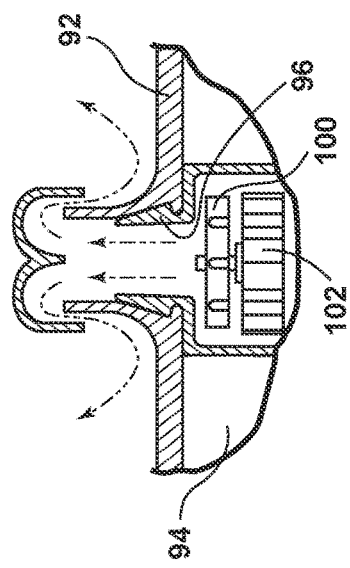
FIG. 16 is another cutaway detail illustration of the connection point between the agitator drum and the base of the third embodiment device, showing the agitator drum removed from the upwardly projecting connection point.
Figure 18:
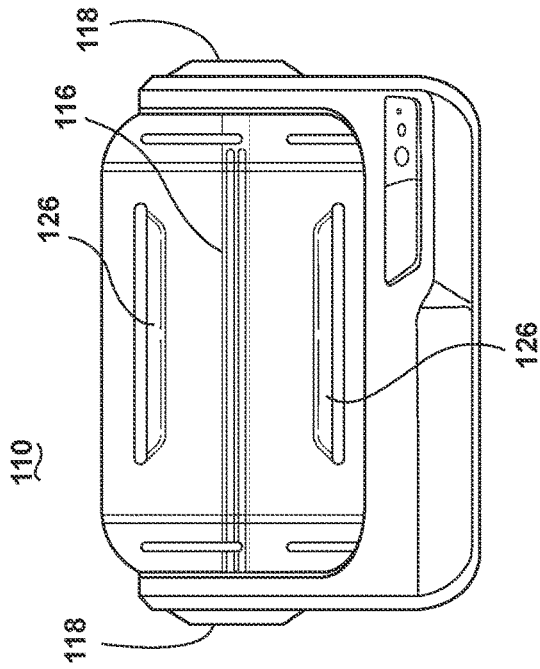
FIG. 18 is a front view of the fourth embodiment of the ultraviolet treatment device described herein.
Figure 17:
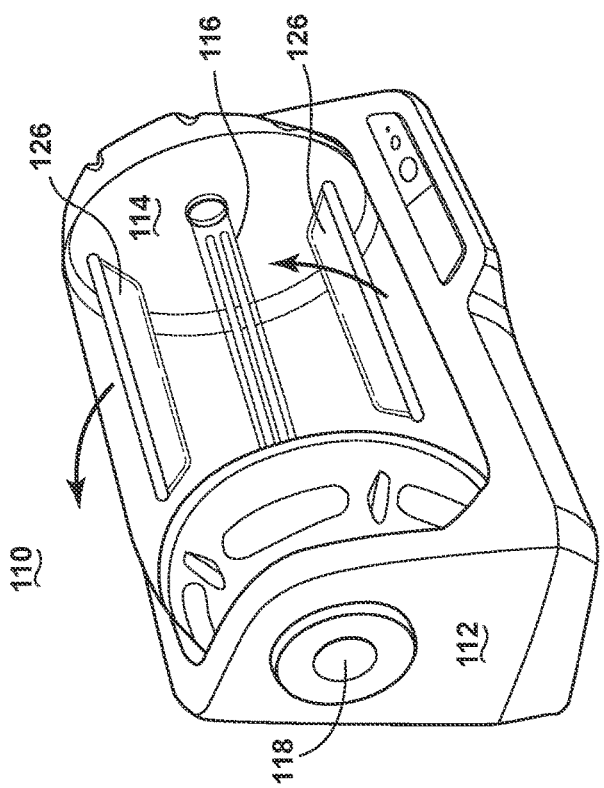
FIG. 17 is a perspective view of a fourth embodiment of the ultraviolet treatment device described herein, with arrows indicating an axis of rotation of the agitator drum.
Figure 19:
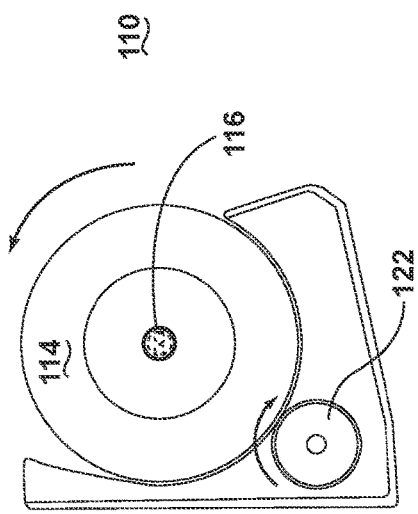
FIG. 19 is a cutaway side schematic view of the fourth embodiment of the ultraviolet treatment device described herein, with arrows indicated the axis of rotation for the agitator drum and an opposite axis of rotation for a smaller diameter drive spindle.

FIG. 15 illustrates an upwardly projecting connection point 96 between the drum 92 and the base 94 of the third embodiment device 80. This connection point 96 enables injection of air or other treatment gas, shown in dashed lines, into the drum 92, through an opening and out of a connection collar 98. This air or other treatment gas may be driven into the drum 92 by the operation of a rotatable propeller 100 operated by a propeller motor 102 or any other gas propulsion system such as compressed air tanks or other pump or pressure generating devices. FIG. 16 shows the drum 92 removed from the upwardly projecting connection point 96. FIG. 16 also serves to illustrate that, in certain embodiments, the drum, or even the entire device, may be tilted to increase the amount of agitation of the agricultural products within the drum.

With respect to FIGS. 17-22 a fourth embodiment of the ultraviolet treatment device 110 is shown. The fourth embodiment of the ultraviolet treatment device 110 includes a base 112, a drum 114, a central UV light source 116, mounts 118 for the drum 114, controls 120, a motor (not shown) and a drive spindle 122 for causing the drum 114 to rotate, with arrows indicating an axis of rotation of the drum 114 and the drive spindle 122. Inserts of plastic 126 added into the interior of the drum 114 to allow control of movement of agricultural products while the drum 114 is rotating. Inserts 126 can include elevations of the surface of the drum 114 or ridges added to the drum 114. Fins, obstacles and other inserts can be used as well, and such inserts 126 can be removable, or repositionable to enable the desired level of agitation.

Because the central UV light source 116 is in the center of the drum 114, the surface of the drum 114 can be altered. If lettuce or other damp material is used, the surface of the containment vessel can be ridged, corrugated, pock-marked, coated, or otherwise configured to prevent material from adhering to the containment vessel walls as it turns or as gas is injected into the containment chamber.

Figure 20:
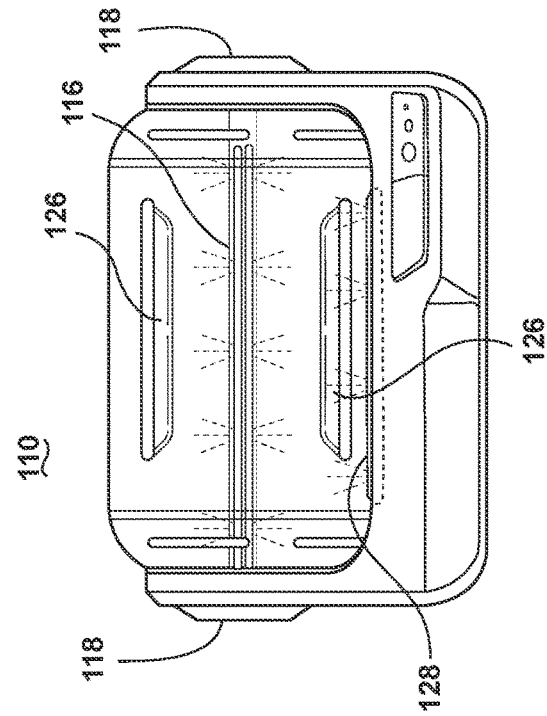
FIG. 20 is a perspective view of the fourth embodiment of the ultraviolet treatment device described herein, further illustrating a supplemental UV light source (or other supplemental light source of another wavelength) outside of the agitator drum, in the base of the device, with dashed lines indicating UV light emanating from the central UV light source and the supplemental UV light source outside of the agitator drum, and with arrows indicating an axis of rotation for the agitator drum.
Figure 21:
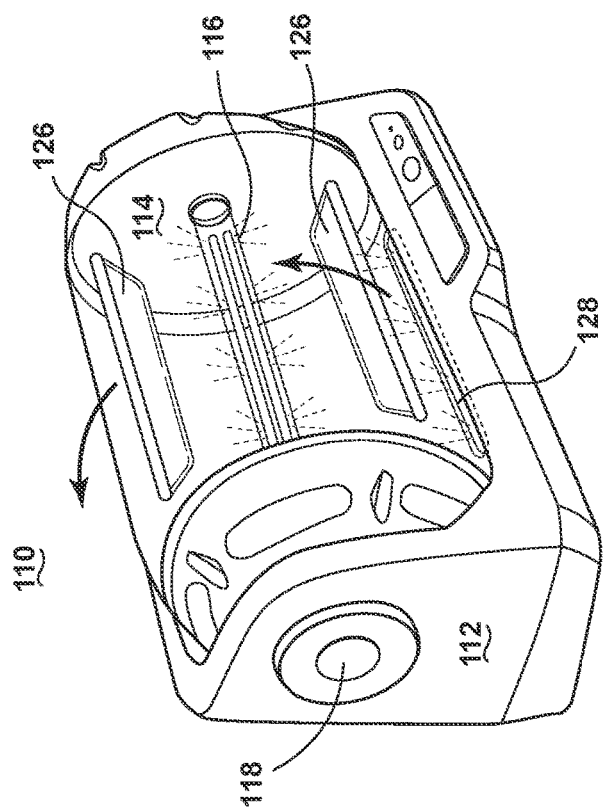
FIG. 21 is a front view of the fourth embodiment of the ultraviolet treatment device described herein, with the supplemental UV light source outside of the agitator drum, in the base of the device, with a dashed line cutaway showing the location of the supplemental UV light source, and other dashed lines indicating UV light emanating from the central UV light source and the supplemental UV light source outside of the agitator drum.
Figure 22:
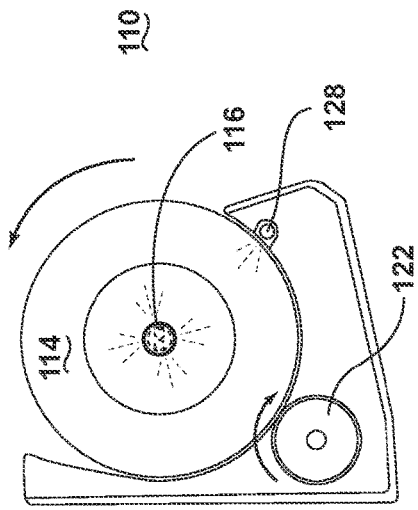
FIG. 22 is a cutaway side schematic view of the fourth embodiment of the ultraviolet treatment device with the supplemental UV light source described herein, with dashed lines indicating UV light emanating from the central UV light source and the supplemental UV light source outside of the agitator drum, and with an arrow indicating the axis of rotation for the agitator drum and an arrow indicating the opposite axis of rotation for the smaller diameter drive spindle.

FIGS. 20-22 illustrating a configuration of the fourth embodiment 110 with a supplemental light source 128 outside of the drum 114, in the base 112 of the device, with dashed lines indicating UV light emanating from the central UV light source 116 and the supplemental light source 128 outside of the drum 114, and with arrows indicating an axis of rotation for the drum 114. The supplemental light source 128 may emit UV light, visible light, or infrared light. As such, it may be used to further modify and control the UV exposure, light exposure and/or temperature of the environment inside the drum 114, and thus the aging, curing, sterilization or other treatment of any agricultural products inside the drum 114. In some alternatives, the supplemental light source 128 is a supplemental UV light source that emits a wavelength that can pass through the material of the drum 114, and may be a different wavelength than the UV light emitted by the central UV light source 116, thereby allowing the agricultural products in the drum 114 to be exposed to different wavelengths of UV light, and different intensities, at the same time. The direction and intensity of any radiation source located on the outside of the drum would be substantially altered and diminished by any irregularity in the surface of the drum. The central radiation source intensity is unaffected.

In most of the embodiments disclosed, the drum is shown as being rotatable around 360 degrees. That said, the rotation can be back and forth by any number of degrees such as 45 clockwise and 45 counter clockwise. In this configuration such rotation would allow agitation without requiring complete rotation.

Figure 24:
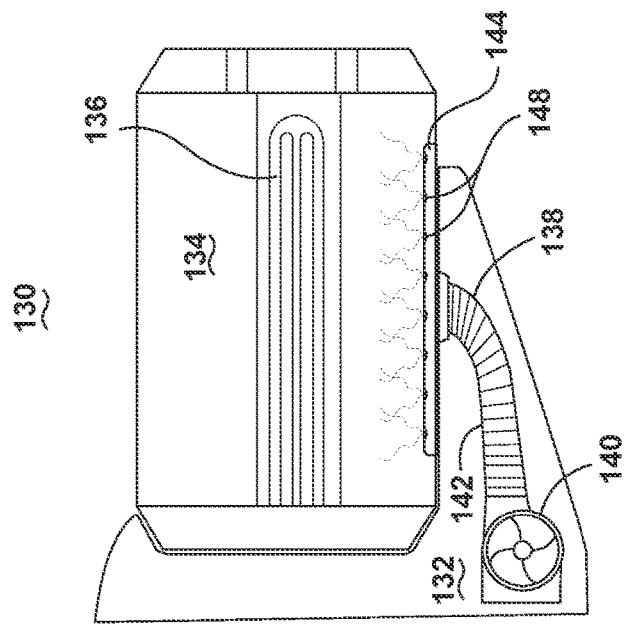
FIG. 24 is a side schematic view of the fifth embodiment of the device with the forced gas agitation mechanism, with light small dotted lines showing forced gas entering the drum.
Figure 23:
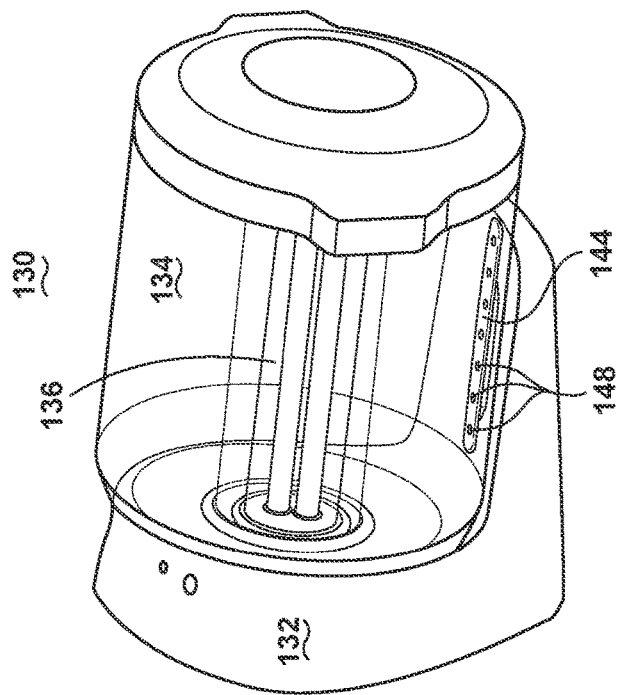
FIG. 23 is a perspective view of a fifth embodiment of the ultraviolet treatment device, with a forced gas agitation mechanism.
Figure 25:
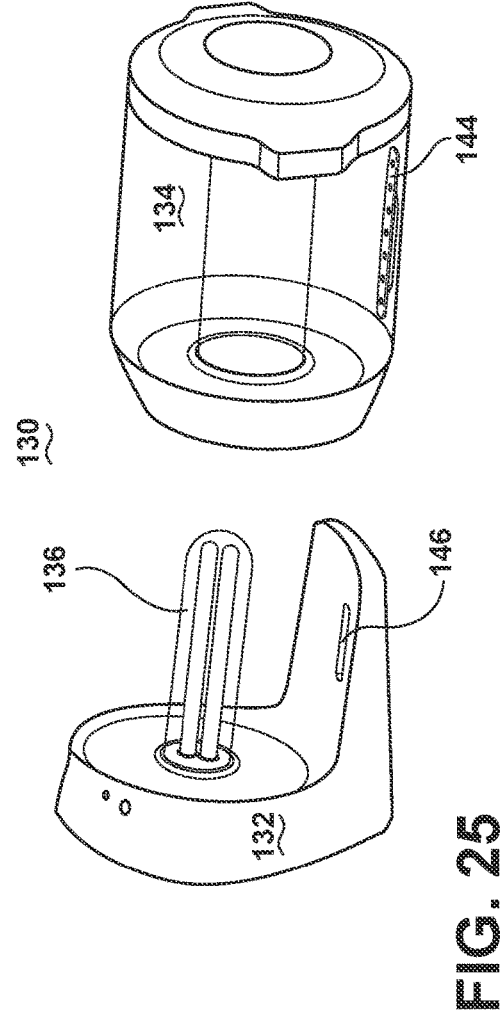
FIG. 25 is a side view of the fifth embodiment of the device showing the drum removed from the base.

With respect to FIGS. 23-25, a fifth embodiment of the ultraviolet treatment device 130 is shown. The device 130 includes a base 132, a drum 134, a central UV light source 136, and a forced gas agitator mechanism 138. The device 130 differs from previous embodiments in that the drum 134 is held stationary with respect to the base 132, while the central UV light source 136 rotates. In some alternatives, not shown, paddles or other mechanical agitation devices may be mounted on or integral to the central UV light source 136. As shown, the device 130 includes a forced gas agitator mechanism 138, including a gas forcing mechanism 140, such as a fan or regulator for pressurized gas, a duct 142, which terminates in an aperture 146, that is in gas-tight communication with a gas ingress vent 144 in the drum 134. The gas ingress vent 144 may have holes 148, or slats, louvers, or other openings for allowing gas to enter the drum 134 and directing the force of the gas entry in order to agitate the agricultural materials in the drum 134. In some embodiments, the drum 134 is gas-tight, to conserve non-atmospheric gases such as purified nitrogen, argon, oxygen, carbon dioxide, etc., and to enable the agricultural products to be placed under gas pressure greater than one atmosphere. In other embodiments, the drum 134 is semi-gas permeable, or "leaky" to allow some gas to escape, thereby avoiding an increase in pressure.

With respect to FIGS. 26-28, a sixth embodiment of the device 150 is shown, illustrating an integrated drum lid/light fixture/forced agitation gas pathway. The device 150 includes a lid mechanism 152, and a drum 154. The lid mechanism 152 includes a latch mechanism/handle 156, a central UV light source 158, contained within a protective column 160, and a ventilation mechanism 162, including a motor or regulator and/or a fan. In operation, the ventilation mechanism 162 can drive gas or air down the protective column 160, in the direction shown by the dotted arrows, and out of a gas ingress vent 164 located at the distal end of the protective column 160, and thus into the drum 154 to agitate and/or treat agricultural products in the drum 154. This embodiment of the device 150 also enables rapid changing of combinations of multiple lid mechanisms 152 and drums 154 prepared with agricultural products, so that drums can be quickly treated, or swapped, as needed to achieve any particular treatment or aging process. The central UV light source 158 and the ventilation mechanism 162 can also be easily accessed for maintenance or modification by opening an access cap 166. FIG. 29 illustrates that multiple, identically shaped drums 154 can be readied in advance with agricultural product, for attachment to the working portion of the device 150.

In connection with this device 150, and/or a number of the other embodiments disclosed herein, a long device can be made by mounting multiple lamps in the center spindle where the lamps are housed. The lamps can be wired sequentially so that energy is passed from the first bulb and electricity to run the lamps is then run through the central spindle to multiple additional lamps if necessary. The central spindle can contain many wires, each wire going to the next lamp, so that each lamp has its own power supply. There would be a rigid central rod of either metal, plastic or other rigid material. Along the rod would pass electrical wiring for each lamp. The lamps would be mounted on the rod. Many lamps could be attached in succession creating a long containment canister.

Figure 31:
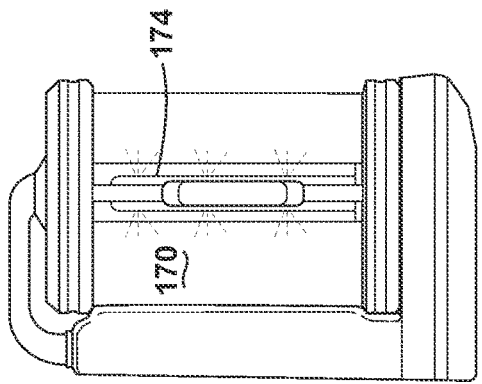
FIG. 31 is a side view of the seventh embodiment of the device, with dashed lines showing UV light emanating from the central light source and a spiral dotted line showing air being drawn through the drum.
Figure 32:
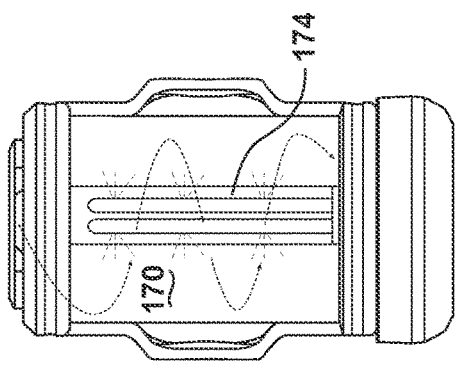
FIG. 32 is a side view of the seventh embodiment of the device without forced air.
Figure 30:
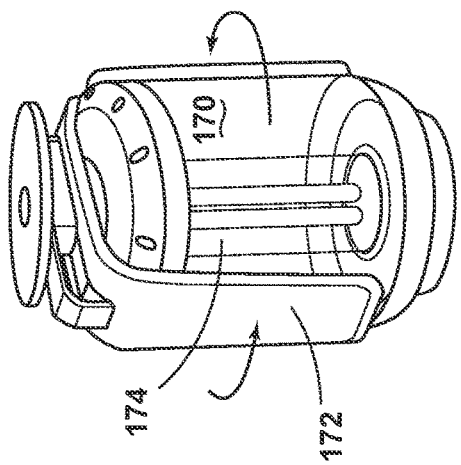
FIG. 30 is a perspective view of a seventh embodiment of the device, with arrows showing an axis of rotation of the drum.

With respect to FIGS. 30-32, three variations of a seventh embodiment of the device 168 is shown, with arrows showing an axis of rotation of the drum 170 affixed to or placed on a base 172, with a central UV light source 174 and various mechanical and gas agitation mechanisms. FIG. 31 is a side view of the seventh embodiment of the device 168, with dashed lines showing UV light emanating from the central light source 174 and a spiral dotted line showing air being drawn through the drum 170. FIG. 32 is a side view of the seventh embodiment of the device 168 without forced air.

Figure 34:
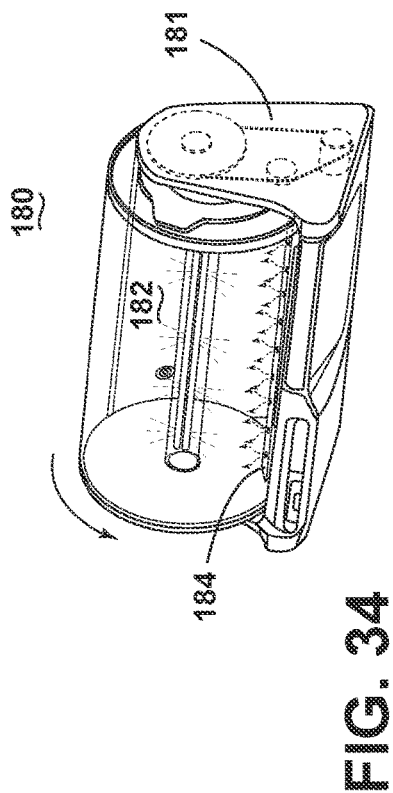
FIG. 34 is a side view of the eighth embodiment of the device, with an axis of rotation of the drum shown by an arrow, UV light emanating from the central light source shown by dashed lines, and forced gas agitation/treatment gas shown entering at the bottom of the drum in dashed lines.
Figure 33:
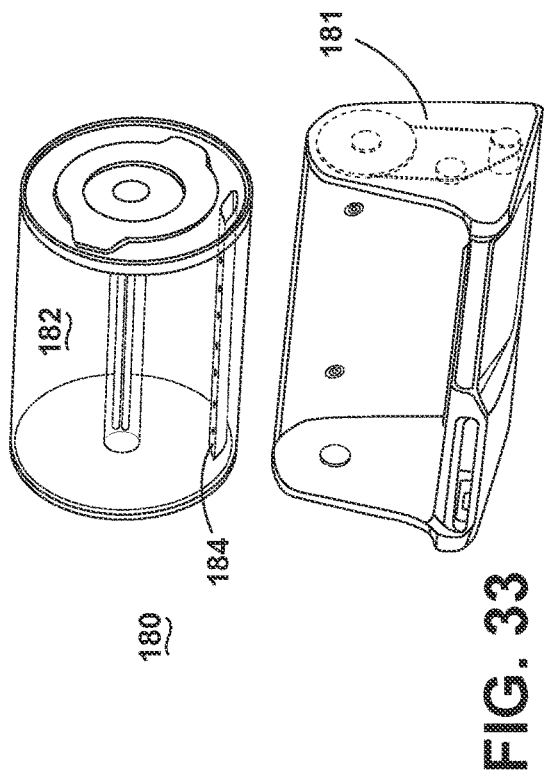
FIG. 33 is a side view of an eighth embodiment of the device, with mechanical agitation by rotation, and forced air agitation, with the drum shown in a removed position and the internal rotation mechanism of the right side of the base shown in dashed lines.

With respect to FIGS. 33-34, an eighth embodiment of the device 180 is shown, with mechanical agitation by rotation of a drum 182, removably mounted on the base 181, and forced air agitation via a gas ingress vent 184 on the drum 182. In this embodiment of the device 180, the gas will be injected for agitation when the gas ingress vent 184 is lined up with the gas aperture on the base with the drum 182. This can occur as a rotation occurs, with the drum 182 remaining in continuous rotational movement. Or, the drum 182 can be held stationary for a period of time to allow gas agitation, followed by (or preceded by, or intermittently) mechanical agitation by rotation of the drum 182.

Figure 35:
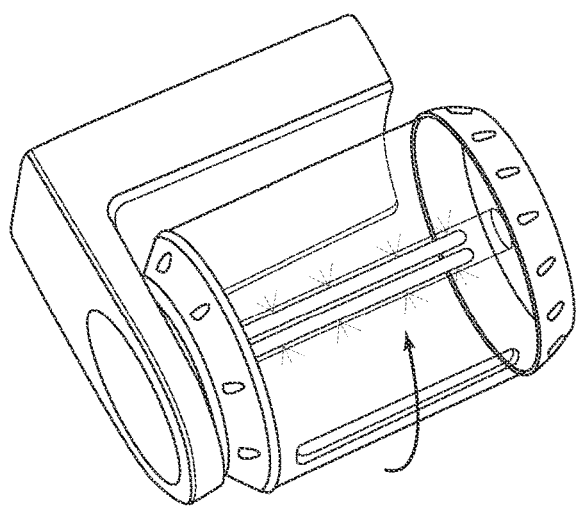
FIG. 35 is a side view of a ninth embodiment of the device, with an axis of rotation of the drum shown by an arrow and UV light emanating from the central light source shown by dashed lines.

FIG. 35 is a side view of a ninth embodiment of the device, with an axis of rotation of the drum shown by an arrow and UV light emanating from the central light source shown by dashed lines.

Figure 36:
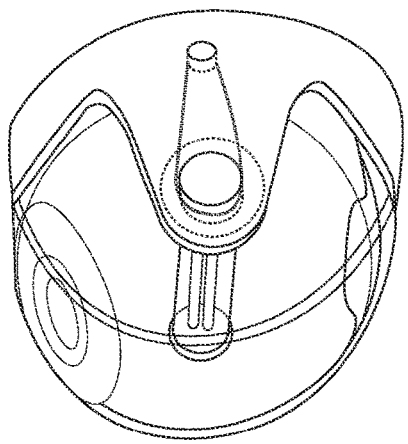
FIG. 36 is a perspective view of an embodiment of the device illustrating that the drum can be mounted in such a way as to allow it to be tipped backwards and forwards along its longitudinal axis to provide further agitation of the agricultural products, in addition to agitation provided by rotation of the drum and gas agitation.

With respect to FIG. 36, an embodiment of the device is illustrated to show that the device can be mounted in such a way that the canister can be tipped backwards and forwards to agitate the material even more than just rotating the material. So as the cylinder is rotating either part or all the entire mechanism can be rocked along its longitudinal axis to further distribute the material within the drum.

Figure 38:
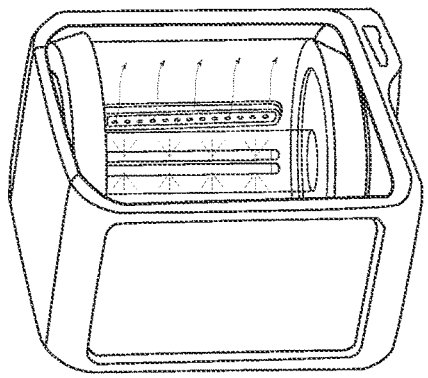
FIG. 38 is a perspective view of the tenth embodiment of the device, with an axis of rotation of the drum shown by dotted arrows and UV light emanating from the central light source shown by dashed lines.
Figure 37:
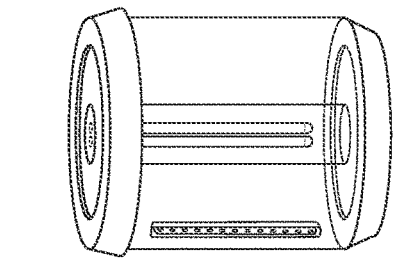
FIG. 37 is a perspective view of a tenth embodiment of the device, with the drum removed.

With respect to FIGS. 37-38 show a tenth embodiment of the device, with an axis of rotation of the drum shown by dotted arrows and UV light emanating from the central light source shown by dashed lines, and gas treatment entering through a gas ingress vent, similar to other disclosed embodiments.

Figure 39:
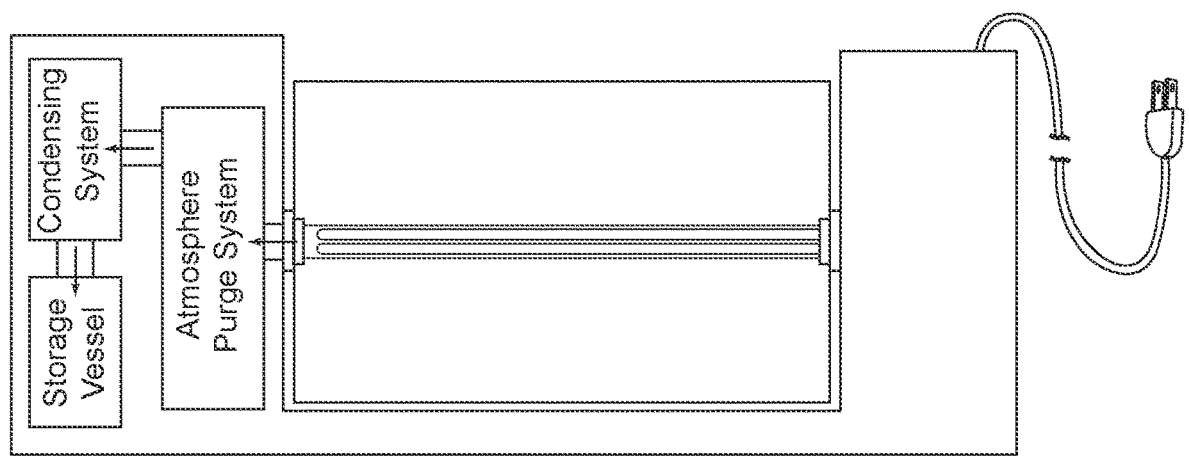
FIG. 39 is a schematic diagram of a forced gas injection and temperature control system, with a capture system for outgoing gas, which may be used with any of the disclosed embodiments.
Figure 40:
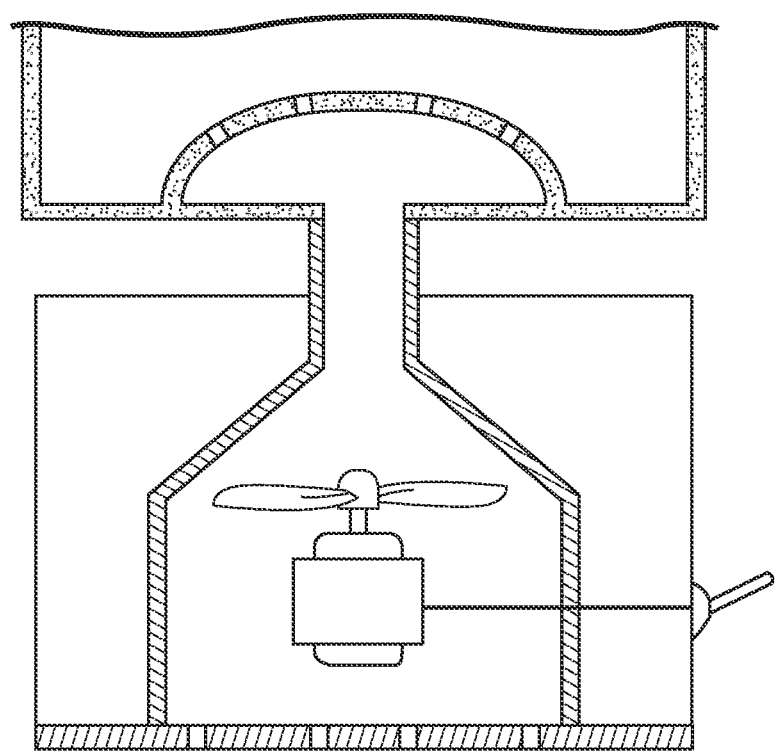
FIG. 40 is a schematic diagram of a close up of the forced gas injection and temperature control system.
Figure 41:
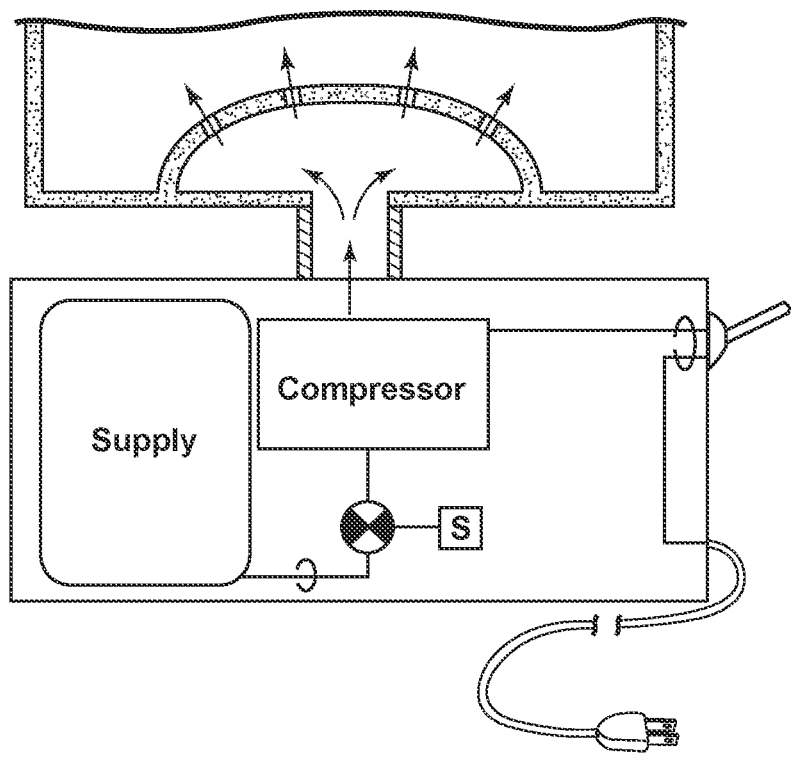
FIG. 41 is a schematic diagram of an alternative embodiment of a forced gas injection and temperature control system, which may be used with any of the disclosed embodiments.
Figure 42:
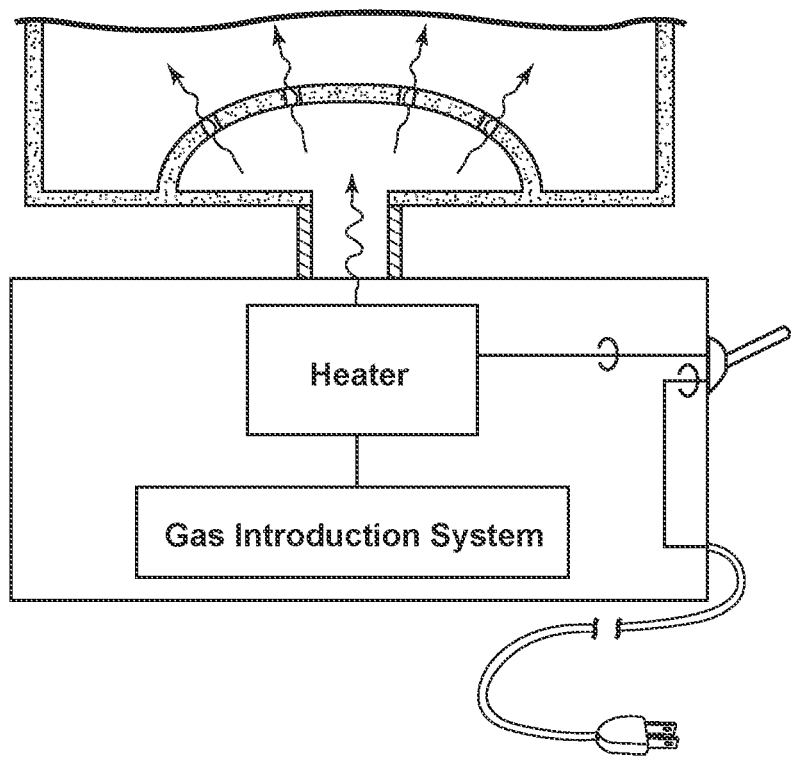
FIG. 42 is a schematic diagram of another alternative embodiment of a forced gas injection and temperature control system, which may be used with any of the disclosed embodiments.
Figure 43:
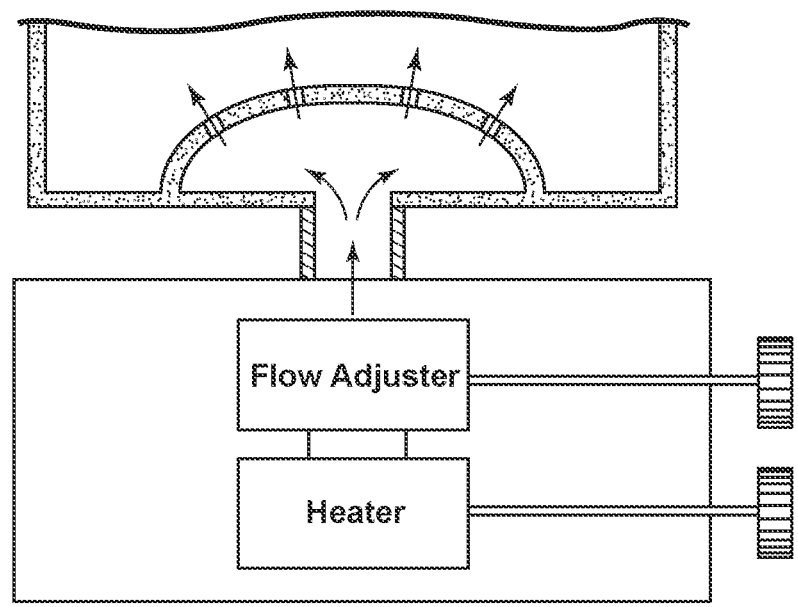
FIG. 43 is a schematic diagram of a still further alternative embodiment of a forced gas injection and temperature control system, which may be used with any of the disclosed embodiments.

WITH RESPECT TO FIG. 39, a schematic diagram of a forced gas injection and temperature control system, with a capture system for outgoing gas, which may be used with any of the disclosed embodiments. This capture system may be useful for various agricultural products that create or release volatile or aromatic compounds during aging or treatment, where these volatile or aromatic compounds are of value. For example, during the treatment of cannabis, especially when temperature is controlled, terpenes are released from the plant. This embodiment shows a capture system for capturing the outgoing gas where it can be run through a condensing system to capture the terpenes and any other gaseous material released from the plant material during treatment.

Figure 44:
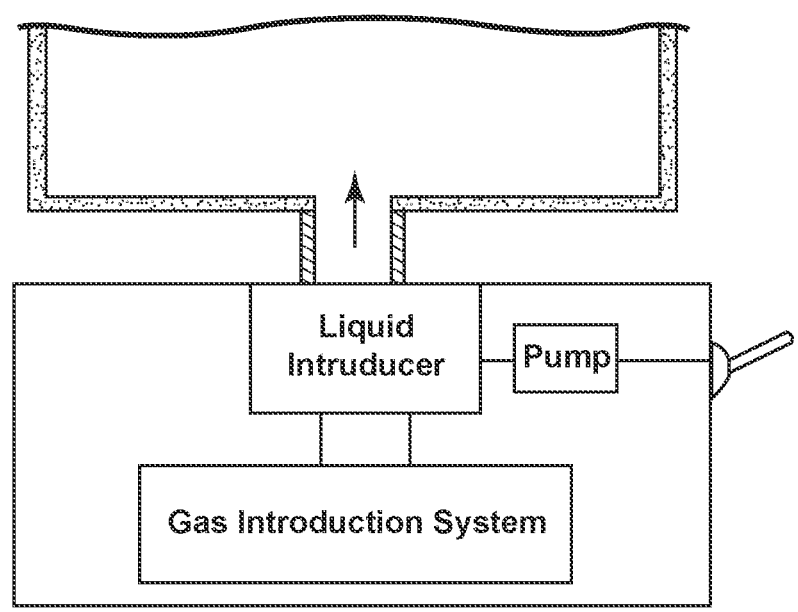
FIG. 44 is a schematic diagram of a still further alternative embodiment of a forced gas injection and temperature control system, which may be used with any of the disclosed embodiments.

With respect to FIGS. 40-44, schematic diagrams of various gas injection and temperature control configurations are provided. The actual inflow shown can be either a single inflow or the inflow can be divided into multiple inflows that may be attached to the bottom of the device shown in FIG. 6. These embodiments show a controlled supply of gas with or without a heating element. A heating element can be added. Gas can also be introduced and eliminated through the central spindle. FIG. 44 illustrates a liquid introduction system. The liquid may represent another chemical compound designed to alter the chemical composition of the material or it may be material for washing, killing various insects, or other indications.

Figure 45:
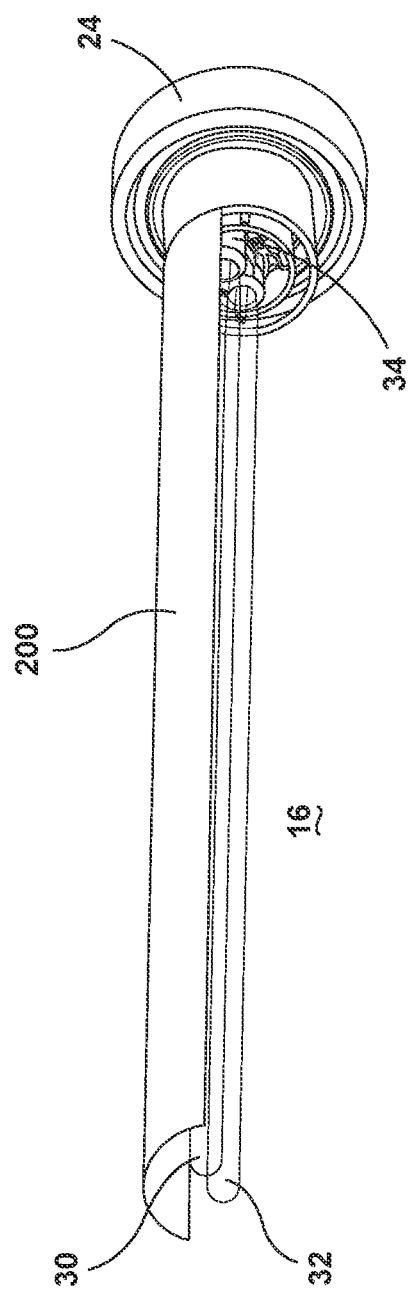
FIG. 45 is a perspective view illustrating an embodiment of the central environmental control unit, which may be used in place of a central spindle for a rotary processing device for plant materials.
Figure 46:
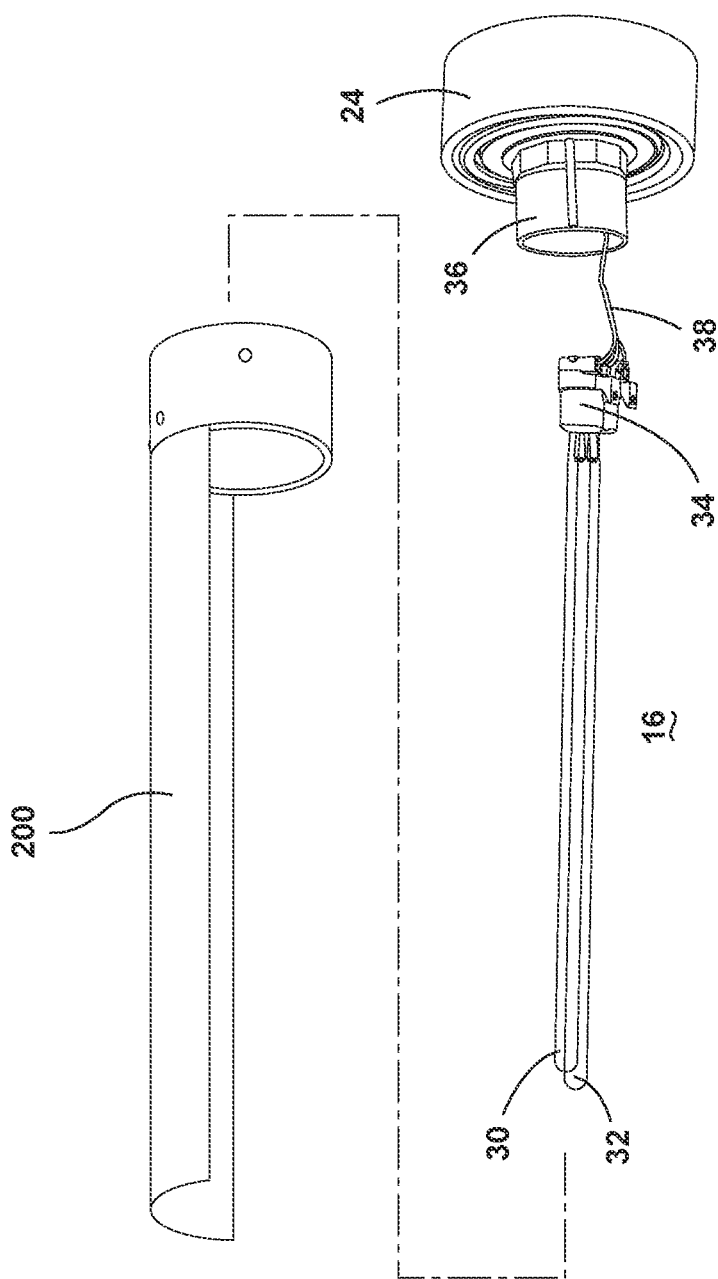
FIG. 46 is an assembly drawing of the central environmental control unit of FIG. 45.
Figure 47:
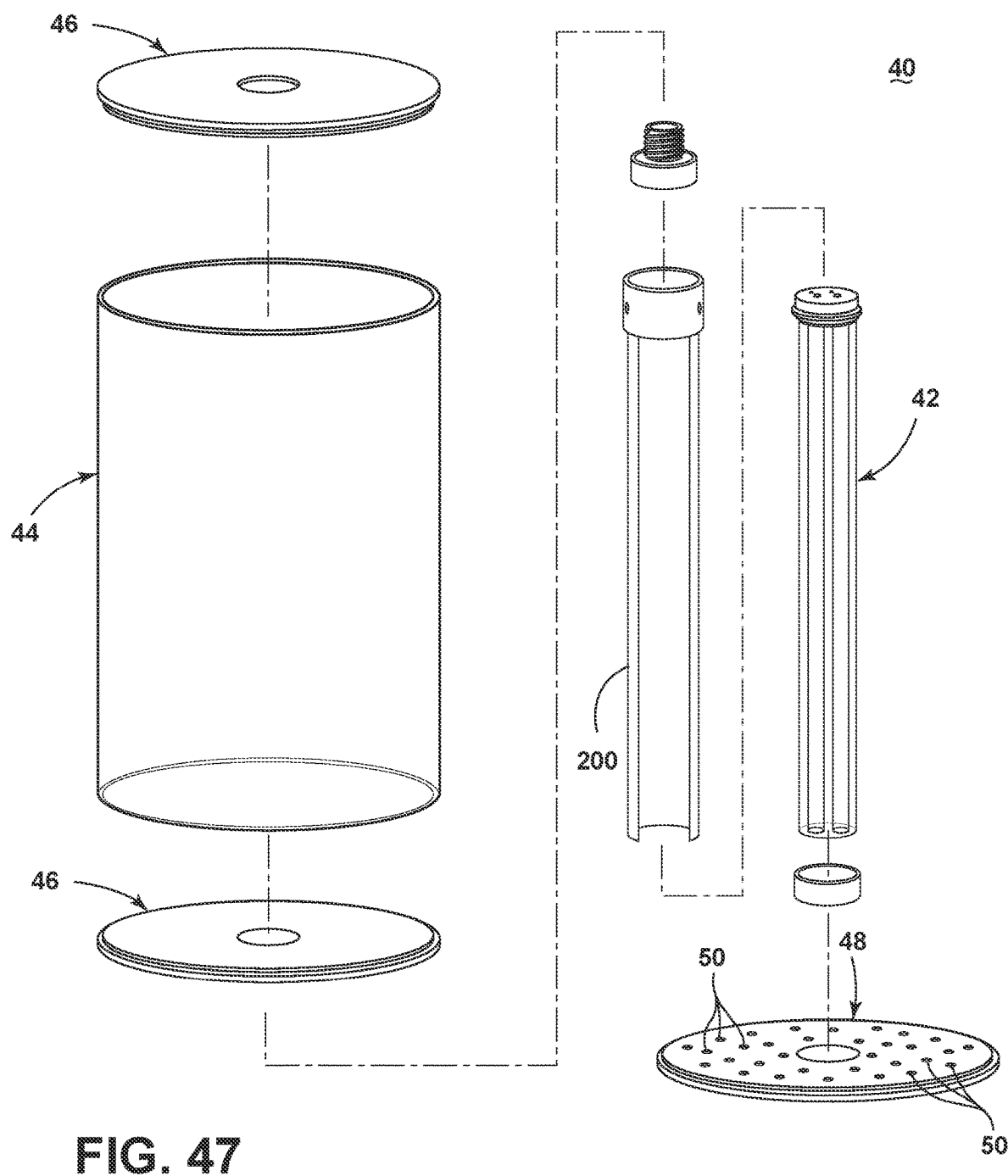
FIG. 47 is an assembly drawing of the central environmental control unit of FIG. 45, illustrating assembly of the central environmental control unit in a rotary drum.

With reference to FIGS. 45-47, a further embodiment of the environmental control unit and drum apparatus is shown. The bearing 24, as well as the mount are constructed of metal, for durability when used for extended periods of time, such as up to 24 hours of continuous rotation by an attached motor (not shown). The device also includes an option metal shield 200 for the UV bulbs. The shield 200 serves to protect the top of the bulbs 30, 32 from being showered with plant material when the device is in operation and the plant material is being agitated, either by mechanical agitation elements or by gaseous or fan agitation elements as described in other embodiments. The top of the shield 200 is preferably curved or angled, so as to allow the shield 200 to shed any plant material that is showered onto it. The metal shield 200 also serves as a reflector, to redirect upwardly travelling UV light back downward, so as to create larger and more efficient UV light delivery to the plant material being agitated in the bottom of the drum 44.

While a number of different embodiments have been illustrated and disclosed herein, it will be understood that the core environmental control unit, such as that shown in FIG. 45, may be used with, or included in the modified design for, many different rotary devices for the processing of plant material. Generally, any rotary processing device that includes a central spindle can be modified to accommodate the environmental control unit shown herein, so as to use the environmental control unit as part of the central spindle and to deliver light or gas exposure to the plant material that is otherwise being processed. An example of such a use is adding the core environmental control unit to any of the various rotary "trimmers" that are in use in the cannabis industry.

Embodiments of the environmental control unit disclosed can be used to connect together as multiple UV light/gas treatment columns, each with a rotational bearing with multiple treatment containers. This multiple-treatment chamber embodiment the device consists of multiple copies of a treatment container (otherwise referred to herein as a drum or a cylinder), with, at one or both ends of the treatment container, a central hole that allows the insertion of a rotational bearing. The bearing allows the treatment container to rotate while the innermost ring of the bearing remains stationary. The environmental control unit is attached to the bearing, allowing the treatment container to rotate while the environmental control unit remains stationary.

Each environmental control unit can contain both a UV or other light source and a gas source. The combination of gas and light can be done through one unit. Ozone blocks UV light for instance in the mixture of light and gas can be problematic. Furthermore we do not know if sequential exposure or simultaneous exposure to various wavelengths of light will make a difference. For that reason the device is constructed for both a single environmental control unit or multiple sequential units.

By linking one or more treatment containers together there is a central pathway down the middle of the cylinders through which the environmental control device can be passed. Alternatively, multiple cylinders and multiple environmental control units may be linked and affixed to one another.

In the first embodiment of this multi-unit device, the cylinders are linked together. The central environmental control device passes into the first cylinder for exposure of light, gas, or other atmospheric control device. After a specific period of time the second environmental control device is attached to the first device. The environmental control devices are passed from the first cylinder to the second cylinder. After specific period of time the third device can be passed. This can go on indefinitely until all of the cylinders have been exposed to atmospheric controls. The central devices advance forward in the first devices disconnected in the process can start again.

Each cylinder is attached to the next cylinder. Each of the environmental control devices can be attached to each other. The first environmental control device is inserted into the first cylinder. The cylinders can either turn individually using a roller system or they all turn together. After a specific period of time the next environmental control device is attached to the first and advanced forward so that the first two cylinders have the device in place. When the first environmental control device reaches the end of the cylinder chain it is detached. The environmental control devices are advanced through the entire system exposing each cylinder to each environmental control device.

The cylinder can be have small holes over the entire surface. Air is forced through the holes to improve agitation of the material within the chamber.

Finally, with reference to the chart incorporated by reference from Cheverfils, the UV dosage required to destroy a virus, bacteria or other contaminant varies from pathogen to pathogen. In the present embodiments, the dose of the UV light can be measured within the treatment container. The dose is known for a given bulb at a given distance. With that information the time of exposure and rotation needed to destroy any given pathogen on treated plant materials can be calculated. In any event, present embodiments may be manufactured from metal, and incorporate highly reliable electric motors, so that with this rugged design, the device may be operated continuously for over twenty-four hours, in order to destroy some of the most difficult to sterilize fungi.

The light from certain bulbs varies by wavelength. The larger the container, the greater the distance between the bulb and the material. The bulbs have a limited length. For large amounts of material multiple smaller containers can be linked together to overcome the limitation of container size. With a central core, containers can be added at one end and removed at the other end. Bulbs can vary in wavelength as well.

Further, embodiments include a two-sided environmental control core that can have lights at both ends for use with a longer barreled treatment container.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments disclosed.

Insofar as the description above discloses any additional subject matter that is not within the scope of the claims below, the inventions are not dedicated to the public and the right to file one or more applications to claim such additional inventions is reserved.

What is claimed is:

1. An ultraviolet light treatment device for treating agricultural products comprising:

an environmental control unit comprising:

a bearing comprising an inner race, an outer race, and a plurality of rotational bearing elements engaged therebetween, wherein the bearing has an axis of rotation;

wherein the inner race includes an aperture;

a mount affixed to the inner race;

an electrical element for positioning and powering an ultraviolet light device, wherein the electrical element is affixed to the mount, such that when the ultraviolet light device is positioned, the ultraviolet light device will be generally parallel to the axis of rotation and projecting away from a first side of the bearing; and an electrical cable, in electrical communication with the electrical element, wherein the electrical cable passes through the aperture and away from a second side of the bearing;

a treatment chamber into which agricultural products may be placed;

wherein the environmental control unit is mounted on the treatment chamber;

wherein the first side of the bearing is positioned toward an interior of the treatment chamber, and the second side of that the bearing is positioned toward an exterior of the treatment chamber, such that the mounted bearing enables the environmental control unit to remain in a fixed position while the treatment chamber may rotate along the axis of rotation to enable agitation of the agricultural products, whereby when the ultraviolet light device is mounted and powered, the agricultural products inside the treatment chamber will be exposed to UV light while being agitated in the treatment chamber.

2. The ultraviolet light treatment device of claim 1 wherein the ultraviolet light device is a UV light bulb.

3. The ultraviolet light treatment device of claim 1 wherein the ultraviolet light device is a plurality of UV LED's.

4. The ultraviolet light treatment device of claim 1 further comprising:

a reflective element configured so as to reflect ultraviolet radiation downward toward the bottom of the treatment chamber.

5. The ultraviolet light treatment device of claim 4 wherein the reflective element is mounted on the mount.

6. The ultraviolet light treatment device of claim 1 wherein the treatment chamber includes a plurality of perforations.

7. The ultraviolet light treatment device of claim 1 wherein the treatment chamber further comprises a mechanical agitation element.

8. The ultraviolet light treatment device of claim 7 wherein the mechanical agitation element is removable.

9. The ultraviolet light treatment device of claim 7 wherein the mechanical agitation element is repositionable.

10. The ultraviolet light treatment device of claim 7 wherein the mechanical agitation element comprises one or more of: a paddle, a screw auger, a tine, a fin, or a scoop.

11. The ultraviolet light treatment device of claim 1 wherein the treatment chamber has an inside surface, and wherein the inside surface is configured with a surface treatment to prevent agricultural materials from adhering to the inside surface.

12. The ultraviolet light treatment device of claim 11 wherein the surface treatment is selected from the group consisting of: ridges, corrugations, pock-marks, and coatings.

13. The ultraviolet light treatment device of claim 1 wherein the treatment chamber is comprised of Plexiglas.

14. The ultraviolet light treatment device of claim 1 further comprising:
a heating element for heat treatment of agricultural products in the treatment chamber.

15. The ultraviolet light treatment device of claim 1 further comprising a rotatable propeller for directing gas flow within the treatment chamber.

16. The ultraviolet light treatment device of claim 1 further comprising a forced gas agitation mechanism.

17. The ultraviolet light treatment device of claim 1 further comprising a forced gas injection and temperature control system.

* * * * *